(12) United States Patent
Woodhouse et al.

(10) Patent No.: US 11,168,371 B2
(45) Date of Patent: Nov. 9, 2021

(54) COMPUTATIONAL METHOD FOR DETECTING FUSION EVENTS

(71) Applicant: Inivata Ltd., Cambridge (GB)

(72) Inventors: Samuel Woodhouse, Cambridge (GB); Stefanie Lensing, Cambridge (GB); Tim Forshew, Stevenage (GB); Vincent Plagnol, Cambridge (GB); Matthew Edward Smith, Cambridge (GB); Karen Howarth, Cambridge (GB); Michael Epstein, Cambridge (GB)

(73) Assignee: INIVATA LTD., Cambridge (GB)

(*) Notice: Subject to any disclaimer, the term of this patent is extended or adjusted under 35 U.S.C. 154(b) by 141 days.

(21) Appl. No.: 16/389,596

(22) Filed: Apr. 19, 2019

(65) Prior Publication Data

US 2019/0241978 A1   Aug. 8, 2019

Related U.S. Application Data

(63) Continuation of application No. PCT/GB2018/051688, filed on Jun. 18, 2018.

(30) Foreign Application Priority Data

Jun. 16, 2017 (GB) .................................... 1709675

(51) Int. Cl.
*C12Q 1/6853* (2018.01)
*C12Q 1/686* (2018.01)
(Continued)

(52) U.S. Cl.
CPC ......... *C12Q 1/6886* (2013.01); *C12Q 1/6806* (2013.01); *C12Q 1/686* (2013.01);
(Continued)

(58) Field of Classification Search
CPC ........ C12Q 2531/113; C12Q 2535/122; C12Q 1/686; C12Q 2600/16; G16B 30/00
See application file for complete search history.

(56) References Cited

U.S. PATENT DOCUMENTS

| 9,145,587 B2 | 9/2015 | Morley |
| 2010/0086918 A1 | 4/2010 | Carson et al. |

(Continued)

FOREIGN PATENT DOCUMENTS

| EP | 1914240 A1 | 4/2008 |
| EP | 2150628 B1 | 12/2013 |

(Continued)

OTHER PUBLICATIONS

Au, C.H. et al., BAMClipper: removing primers from alignments to minimize false-negative mutations in amplicon next-generation sequencing, Scientific Reports, vol. 7: 1567, pp. 1-7 (Year: 2017).*

(Continued)

*Primary Examiner* — Teresa E Strzelecka
(74) *Attorney, Agent, or Firm* — James S. Keddie; Bozicevic, Field & Francis LLP

(57) ABSTRACT

The present disclosure relates to methods for detecting and targeting genomic rearrangements, in particular gene fusion events, by targeting a DNA molecule of interest with a set or pool of primers, wherein the forward primers and reverse primers produce a PCR amplification product when a genomic rearrangement is present. The present disclosure also relates to methods of bioinformatic analysis to determine whether or not the detection of an amplification product from the selective PCR is actually indicative of the presence of a gene fusion. The present disclosure also related to related methods of diagnosis and treatment of (Continued)

diseases and conditions associated with such genomic rearrangements, in particular cancers, such as lung cancer.

12 Claims, 8 Drawing Sheets

Specification includes a Sequence Listing.

(51) Int. Cl.
    *G16B 30/00*    (2019.01)
    *C12Q 1/6886*   (2018.01)
    *C12Q 1/6806*   (2018.01)
    *G16B 20/00*    (2019.01)

(52) U.S. Cl.
    CPC ..... *C12Q 1/6853* (2013.01); *C12Q 2600/106* (2013.01); *C12Q 2600/156* (2013.01); *C12Q 2600/16* (2013.01); *G16B 20/00* (2019.02); *G16B 30/00* (2019.02)

(56) References Cited

U.S. PATENT DOCUMENTS

| | | |
|---|---|---|
| 2015/0315657 A1 | 11/2015 | Rhodes et al. |
| 2016/0275240 A1 | 9/2016 | Huelga et al. |
| 2016/0319365 A1 | 11/2016 | Saffroy et al. |
| 2017/0283854 A1* | 10/2017 | Dervinis .............. C12Q 1/68 |
| 2019/0185913 A1 | 6/2019 | Zimmermann et al. |

FOREIGN PATENT DOCUMENTS

| | | |
|---|---|---|
| WO | WO 2008/144841 A1 | 12/2008 |
| WO | WO 2011/140187 A2 | 11/2011 |
| WO | WO 2015/075196 A1 | 5/2015 |

OTHER PUBLICATIONS

Maher, C.A. et al., Chimeric tranmscript discovery by paired-end transcriptosome sequencing, PNAS, vol. 106, pp. 12353-12358 plus supporting information pp. 1-12 (Year: 2009).*

Levin, J.Z. et al., Targeted next-generation sequencing of a cancer transcriptome enhances detection of sequence variants and novel fusion transcripts, Genome Biol., vol. 10: R115, pp. 1-8 (Year: 2009).*

Kohno, T. et al., Beyond ALK-RET, ROS1 and other oncogene fusions in lung cancer, Transl. Lung Cancer, vol. 4, pp. 156-164 (Year: 2015).*

Shokralla et al., "Next-generation DNA barcoding: using next-generation sequencing to enhance and accelerated DNA barcode capture from sincle specimens" Molecular Ecology Resources, 2014, 14:892-901.

Ajay et al., "Accurate and comprehensive sequencing of personal genomes", Genome Research, 2011, 21(9):1498-1505.

Beadling et al., "A Multiplexed Amplicon Approach for Detecting Gene Fusions by Next-Generation Sequencing", The Journal of Molecular Diagnostics, 2016, 18(2): 165-175.

Dewald et al., "Highly Sensitive Fluorescence In Situ Hybridization Method to Detect Double BCR/ABL Fusion and Monitor Response to Therapy in Chronic Myeloid Leukemia", Blood, 1998, 91(9): 3357-3365.

Duployez et al., "Minimal residual disease monitoring in t(8;21) acute myeloid leukemia based on RUNX1-RUNX1T1 fusion quantification on genomic DNA", American Journal of Hematology, 2014, 89(6): 610-615.

Lawson et al., "RAF gene fusion breakpoints in pediatric brain tumors are characterized by significant enrichment of sequence microhomology", Genome Research, 2011, 21(4): 505-514.

Metzler et al., "Asymmetric multiplex-polymerase chain reaction—a high throughput method for detection and sequencing genomic fusion sites in t(4;11)", Blackwell Publishing Ltd, British Journal of Haematology, 2004, 124: 47-54.

Mooradian et al., "ALK Fusion Detection in Circulating Free DNA: Finding an Important Needle in the Haystack", The Oncologist, 2017, 22:759-761.

Colman, et al.; "Detection of Low-Level Mixed-Population Drug Resistance in *Mycobacterium tuberculosis* Using High Fidelity Amplicon Sequencing"; PLOS ONE; vol. 10, No. 5, 18 pages (May 13, 2015).

Jennings, et al.; "Guidelines for Validation of Next-Generation Sequencing-Based Oncology Panels"; J. Mol. Diagn.; vol. 19, No. 3, pp. 341-365 (May 2017).

Jobbagy, et al.; "Evaluation of the Cepheid GeneXpert BCR-ABL Assay"; J. Mol. Diagn.; vol. 9, No. 2, pp. 220-227 (Apr. 2007).

Kidess, et al.; "Circulating tumor cells versus tumor-derived cell-free DNA: rivals or partners in cancer care in the era of single-cell analysis?"; Genome Medicine; vol. 5, No. 70, 4 pages (2013).

Kohno, et al.; "Beyond ALK-RET, ROS1 and other oncogene fusions in lung cancer"; Transl Lung Cancer Res; vol. 4, No. 2, pp. 156-164 (2015).

Salzman, et al.; "ESRRA-C11 orf20 Is a Recurrent Gene Fusion in Serous Ovarian Carcinoma"; PLoS Biology; vol. 9, No. 9, 9 pages (Sep. 2011).

* cited by examiner

CD74

ROS1

[Insertion]

ROS1-CD74 gBlock Sequence

CGCCAAGGTCACAGCTGCTGCCAAGAGAGCCTTGGGCGTTTCCCACCTCATG
GACAATGCAGACTAGGATGTTTTTAGACCCAAAGACAGAGTGCTGTTTCTATC
CCGGTGCTGTCTCTAATTTGCTATGTAACTTTGGACAAGTCCCCTTCCCTCTAG
GATTCAGGGTCCTGAAGTAGAAGGTCAAAGGGCCACCCTGCCTGGGGCCTC
AGTTTCTGCATCAGATTCATAGAAGGCACCTTACATGCT[AT]TGTCATGTATATT
TTCTGTATTTATTATTTTTTGCAGAAAGAGCACTTCAAATAATTTACAGAACCA
GAATTTAAGGTGGAGATGACATTTAATGGATCCTGCAGTAGTGTTTGCACATG
GAAGTCCAAAAACCTGAAAGGAATATTTCAGTTCAGAGTAGTAGCTGCAAAT
AATCTAGGGTTTGGTGAATATAGTGGAATCAGTGAGAATATTATATTAGTTGGA
GGTATGTTACCATGTCTGTCTA

| Forward Primer | Reverse Primer | Read Sequence |
|---|---|---|
| CD74_E6-I6_10 | ROS1_I32_E33_414 | TTACATGCTATTGTCATGTATATTTCTGTATTATTATTTTGCAGAAAGAGCAC TCAAATAATTACAGAACCAGAATTAAGTGGAAGATGACATTTA |
| CD74_E6-I6_9 | ROS1_I32_E33_414 | CCCTGCCTGGGGCCTCAGTTTCTGCATCAGATTCATAGAAGGCACCTTACATGC TATTGTCATGTATATTTCTGTATTATTATTTTGCAGAAAGAGCACTTCAAAT |

B

CD74_E6-I6_10/ROS1_I32_E33_414 Read

CGCCAAGGTCACAGCTGCTGCCAAGAGCCTTGGCGTTCCCA
CCTTCATGGACAATGCAGACTAGGAGTGTTTTAGACCTCAAAGACAG
AGTGCTGTTCTATTCCGGTGCGTCTCTAATTTGCTATGTAACTTTG
GACAAGTCCCCTTCCCTCTAGGATTCAGGGTCCTGAAGTAGAAGG
TCAAAGGGCACCTGCCTGGGGCCTCAGTTTCTGCATCAGATTCA
TAGAAGGCACCTTACATGCT[AT]TGTCATGTATATTTCTGTATTAT
TATTTTTGCAGAAAGAGCACTTCAAATAATTACAGAACCAGAAT
TAAGGTGGAGATGACATTTAATGGATCCTGCAGTAGTGTTTGCAC
ATGGAAGTCAAAAACTGAAAGAATATTCAGTTCAGAGTAGT
AGTTGCAAATAATCTAGGGTTTGTGTAATAGTGGAATTCAGTGAAG
AATATTATATTAGTTGGAGGTATGTTACCATGTCTGTCTA

CD74_E6-I6_9/ROS1_I32_E33_414 Read

CGCCAAGGTCACAGCTGCTGCCAAGAGCCTTGGCGTTCCCA
CCTTCATGGACAATGCAGACTAGGAGTGTTTTAGACCTCAAAGACAG
AGTGCTGTTCTATTCCGGTGCGTCTCTAATTTGCTATGTAACTTTG
GACAAGTCCCCTTCCCTCTAGGATTCAGGGTCCTGAAGTAGAAGG
TCAAAGGGCACCTGCCTGGGGCCTCAGTTTCTGCATCAGATTCA
TAGAAGGCACCTTACATGCT[AT]TGTCATGTATATTTCTGTATTAT
TATTTTTGCAGAAAGAGCACTTCAAATAATTACAGAACCAGAAT
TAAGGTGGAGATGACATTTAATGGATCCTGCAGTAGTGTTTGCAC
ATGGAAGTCAAAAACTGAAAGAATATTCAGTTCAGAGTAGT
AGTTGCAAATAATCTAGGGTTTGTGTAATAGTGGAATTCAGTGAAG
AATATTATATTAGTTGGAGGTATGTTACCATGTCTGTCTA

CD74  ROS1  [Insertion]  Sequence Read

FIG. 6

SEQUENCE LISTING

```
<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: EML4-ALK gene fusion

<400> SEQUENCE: 1
gaagttccta tactttctag agaataggaa cttc                               34

<210> SEQ ID NO 2
<211> LENGTH: 108
<212> TYPE: DNA
<213> ORGANISM: Artificial Sequence
<220> FEATURE:
<223> OTHER INFORMATION: Primer Set 1

<400> SEQUENCE: 2
ttaattaaat gttttcaaa tccattcacc tgaatgtcta agcttggcag gaagttccta    60
tactttctag agaataggaa cttcggaata ggaacttcat atggtgcc                108

<210> SEQ ID NO 3
<211> LENGTH: 68
<212> TYPE: DNA
<213> ORGANISM: Artificial Sequence
<220> FEATURE:
<223> OTHER INFORMATION: Primer Set 2

<400> SEQUENCE: 3
aggaagttcc tatactttct agagaatagg aacttcggaa taggaacttc atatggtgcc    60
atccctca                                                            68

<210> SEQ ID NO 4
<211> LENGTH: 499
<212> TYPE: DNA
<213> ORGANISM: Artificial Sequence
<220> FEATURE:
<223> OTHER INFORMATION: ROS1-CD74 gBlock Sequence

<400> SEQUENCE: 4
cgccaaggtc acagctgctg ccaagagagc cttgggcgtt tcccacctca tggacaatgc    60
agactaggat gttttagac ccaaagacag agtgctgttt ctatcccggt gctgtctcta    120
atttgctatg taactttgga caagtcccct tccctctagg attcagggtc ctgaagtaga    180
aggtcaaagg gccaccctgc ctgggcctc agtttctgca tcagattcat agaaggcacc    240
ttacatgcta ttgtcatgta tatttctgt atttattatt ttttgcagaa agagcacttc    300
aaataattta cagaaccaga atttaaggtg gagatgacat taatggatc ctgcagtagt    360 gtttgcacat ggaagtccaa aaacctgaaa ggaatatttc agttcagagt agtagctgca    420
```

```
aataatctag ggtttggtga atatagtgga atcagtgaga atattatatt agttggaggt    480
atgttaccat gtctgtcta                                                 499
```

<210> SEQ ID NO 5
<211> LENGTH: 104
<212> TYPE: DNA
<213> ORGANISM: Artificial Sequence
<220> FEATURE:
<223> OTHER INFORMATION: CD74_E6-I6_10 (fw) ROS1_I32_E33_414 (rv)
     sequence read

<400> SEQUENCE: 5

```
ttacatgcta ttgtcatgta tattttctgt atttattatt ttttgcagaa agagcacttc    60
aaataattta cagaaccaga atttaaggtg aagatgaca ttta                      104
```

<210> SEQ ID NO 6
<211> LENGTH: 110
<212> TYPE: DNA
<213> ORGANISM: Artificial Sequence
<220> FEATURE:
<223> OTHER INFORMATION: CD74_E6-I6_9 (fw) ROS1_I32_E33_414 (rv)
     sequence read

<400> SEQUENCE: 6

```
ccctgcctgg ggcctcagtt tctgcatcag attcatagaa ggcaccttac atgctattgt    60
catgtatatt ttctgtattt attatttttt gcagaaagag cacttcaaat               110
```

<210> SEQ ID NO 7
<211> LENGTH: 499
<212> TYPE: DNA
<213> ORGANISM: Artificial Sequence
<220> FEATURE:
<223> OTHER INFORMATION: CD74_E6-I6_10/ROS1_I32_E33_414 Read

<400> SEQUENCE: 7

```
cgccaaggtc acagctgctg ccaagagagc ctgggcgtt tcccacctca tggacaatgc     60
agactaggat gttttagac ccaaagacag agtgctgttt ctatcccggt gctgtctcta    120
atttgctatg taactttgga caagtccct tccctagg attcagggtc ctgaagtaga     180
aggtcaaagg gccaccctgc ctggggcctc agtttctgca tcagattcat agaaggcacc   240
ttacatgcta ttgtcatgta tattttctgt atttattatt ttttgcagaa agagcacttc   300
aaataattta cagaaccaga atttaaggtg gagatgacat ttaatggatc ctgcagtagt   360
gtttgcacat ggaagtccaa aaacctgaaa ggaatatttc agttcagagt agtagctgca   420
aataatctag ggtttggtga atatagtgga atcagtgaga atattatatt agttggaggt   480
atgttaccat gtctgtcta                                                499
```

<210> SEQ ID NO 8
<211> LENGTH: 499
<212> TYPE: DNA
<213> ORGANISM: Artificial Sequence
<220> FEATURE:
<223> OTHER INFORMATION: CD74_E6-I6_9/ROS1_I32_E33_414 Read

<400> SEQUENCE: 8

```
cgccaaggtc acagctgctg ccaagagagc ctgggcgtt tcccacctca tggacaatgc     60
agactaggat gttttagac ccaaagacag agtgctgttt ctatcccggt gctgtctcta    120
atttgctatg taactttgga caagtccct tccctagg attcagggtc ctgaagtaga     180
aggtcaaagg gccaccctgc ctggggcctc agtttctgca tcagattcat agaaggcacc   240
```

```
ttacatgcta ttgtcatgta tattttctgt atttattatt ttttgcagaa agagcacttc      300
aaataattta cagaaccaga atttaaggtg gagatgacat ttaatggatc ctgcagtagt      360
gtttgcacat ggaagtccaa aaacctgaaa ggaatatttc agttcagagt agtagctgca      420
aataatctag ggtttggtga atatagtgga atcagtgaga atattatatt agttggaggt      480
atgttaccat gtctgtcta                                                  499
```

COMPUTATIONAL METHOD FOR DETECTING FUSION EVENTS

CROSS-REFERENCING

This application is a continuation of international Application No. PCT/GB2018/051688, filed on Jun. 18, 2018, which claims the benefit of United Kingdom Application No. GB1709675.1, filed on Jun. 16, 2017, which applications are incorporated herein in their entireties for all purposes.

BACKGROUND

The present disclosure relates to methods for detecting genomic rearrangements, in particular gene fusion events, as well as related methods of diagnosis and treatment of diseases and conditions associated with such genomic rearrangements, in particular cancers, such as lung cancer.

Genetic or chromosomal rearrangements are a type of chromosomal abnormality in which the normal order of the genetic code has been altered. A common genomic rearrangement that is associated with cancer is genetic fusion. A gene fusion event may occur in cancerous or pre-cancerous cells and can be detected in patients to help classify the cancer and determine appropriate treatments.

Existing methods for detecting gene fusions include fluorescence in situ hybridization (FISH), RT-PCR, long range PCR and hybridisation capture followed by next generation sequencing. FISH uses DNA or RNA probes, tagged with targets for antibodies, with fluorophores or with biotin. These probes are applied to an interphase or metaphase chromosome preparation in order to detect either the co-localisation of two genes typically separate in a nuclei or the breaking apart of a genes signal, indicating its fusion to another region of the genome. An example of this approach is the detection of the BCR/ABL fusion by FISH and the use of this to monitor response to therapy in chronic myeloid leukemia (Dewald G W et al. Blood. American Society of Hematology; 1998; 91: 3357-65). FISH can only be applied to cells or tissue and therefore cannot be used to detect gene fusions in cell free circulating nucleic acids or in DNA already extracted from tissue. FISH also requires intact nuclei, the need to visually assess individual cells and cannot give the sequence of the breakpoint.

RT-PCR can be used to amplify the messenger RNA (mRNA) transcript of a fusion gene and specifically detect its presence. Reverse transcription is used to convert RNA to cDNA followed by PCR using fusion specific primers to amplify the fusion of interest. As intronic sequences are spliced out in the generation of mRNA this is relatively simple and typically requires just one pair of primers or a small multiplex of primers. The products of such a PCR can then be detected in multiple ways such as through gel electrophoresis with intercalating agents like ethidium bromide or using a fluorescent probe with real time or digital PCR. For example (U.S. Pat. No. 4,874,853). However, this approach can only be applied to mRNA and it is not feasible to identify the breakpoints that have occurred in the genome (DNA). mRNA typically has a short half-life and is therefore a challenging biomarker in heavily degraded samples such as FFPE and circulating RNA (ctRNA).

An alternative is to directly detect the fusion in genomic DNA. A significant challenge with this approach is that the fusions will often occur throughout large intronic spaces. One solution to this is long range PCR. By using a limited number of primers tiled typically 500 bp to 10,000 bp apart throughout each gene of interest it is possible to setup multiple singleplex PCR reactions in order to amplify the fusion genes (Lawson A R J et al. Genome Res. 2011; 21:505-14; EP1914240; Duployez N et al. Am J Hematol. 2014; 89: 610-615). To reduce the number of reactions required it has been shown that this long-range PCR can be performed in multiplex. Metzler et al developed a multiplex of 25 forward primers and 5 biotinylated reverse primers used to amplify the translocation t(4; 11) followed by positive selection for PCR products containing one of the biotin-labelled primers then a second PCR using additional target specific primers in a method called Asymmetric multiplex PCR (Metzler M et al. Br J Haematol. 2004; 124: 47-54). In this method their primers were typically 1,000 bp apart or greater. The limitation with these approaches is the requirement for DNA greater than 500 bp in length and therefore they are not suitable for fragmented DNA such as FFPE or cfDNA. These long-range PCR methodologies are also not compatible with Next Generation Sequencing Technologies due to the short-read length (<500 bp) of most next generation sequencing platforms without further complex steps such as fragmenting the DNA then ligating on adaptors. This methodology also requires a potentially large number of individual PCR reactions to assess each sample or complex steps such as positive selection using biotin-labelled primers in order to multiplex such a reaction.

Alternatively, targeted enrichment and detection of fusions can be achieved by hybridisation, whereby a biotinylated probe (~120 bases) with complementarity to the target of interest, is hybridised to the DNA under investigation to selectively recover and thus enrich for regions of interest with the use of streptavidin coated magnetic beads. In this case, regions of interest are genomic regions that are known to undergo gene fusions. With this hybridisation approach, genomic regions of interest are recovered whether or not they have undergone a gene fusion event. Thus, significant sequencing capacity is expended decoding such regions even when no fusion event has occurred. Additionally, with this approach, prior to enrichment, DNA has to be extensively processed (consisting of end-repair, A-tailing and ligation). As these steps are highly inefficient ~70% of starting material is lost prior to hybridisation, limiting the ability to detect fusions present at low allelic frequencies. Finally, this approach is time consuming, normally requiring overnight incubation of target and probe to enable hybridisation.

Target enrichment by primer extension enables fusion gene detection with knowledge of only one of the two fusion partners. However, this approach is time consuming and requires the ligation of universal adapters to DNA ends. The inefficiency of ligation limits the ability to detect fusions present at low allelic frequencies. As with a hybridisation approach, genomic regions of interest are recovered whether or not they have undergone a gene fusion event with this approach and thus, significant sequencing capacity is needed to assess these large regions if high sensitivity is required.

US20160319365 discloses methods for detecting chromosomal rearrangements using hybridisation probes. However, such techniques require probes to be designed for the target region, in addition to PCR primers for the target region. Therefore, the likelihood of detecting a fusion event is diminished as an additional enrichment step is performed. It also increases complexity and cost of the workflow as an additional hybridisation probe is required.

There remains in the art a need for a method of detecting gene fusions in an efficient manner, such that gene fusion events can be detected even when they occur at a low allelic frequency, particularly when such fusions occur in highly fragmented genomic DNA.

These and other features of the present teachings are set forth herein.

SUMMARY OF THE INVENTION

The present disclosure relates to methods for targeting genomic rearrangement, in particular gene fusion events, by targeting a DNA molecule of interest with a set or pool of primers, wherein the forward primers and reverse primers produce a PCR amplification product when a genomic rearrangement is present. This is achieved by targeting a first region with the forward primers and targeting a second, different, region with the reverse primers. The forward and reverse primers produce an amplification product when they anneal in sufficient proximity to each other. Hence, an amplification product will be produced when a genomic rearrangement has occurred to bring the first and second regions into sufficient proximity. The amplification product is then sequenced to identify the presence and position of the genomic rearrangement. By combining selective amplification and sequence determination it is possible to identify a genomic rearrangement at low allelic fraction even if the PCR produces off-target amplification. The methods disclosed herein do not require a further enrichment step, such as enrichment comprising hybridisation to a probe. The sequence of a reaction product is indicative of the presence of a genomic rearrangement, since the sequence read can be used to directly detect (and characterise) the fusion. Multiple genomic rearrangements can be detected in a single reaction by using multiple sets or pools of primers to detect the genomic rearrangements, wherein each paired set or pool of primers is designed to amplify a different genomic rearrangement (if present). The methods can also be combined with methods to determine the presence or absence of genetic alterations that are not genomic rearrangements, such as single nucleotide polymorphisms (SNPs). This can be achieved by using additional primer pairs that act both as a positive control and to further characterise a disease or disorder or a patient from whom a sample has been taken and analysed. The present disclosure does not require end repair or ligation to enrich for targets of interest and therefore a further advantage is that there is no loss of starting material due to processing prior to fusion detection.

The methods disclosed herein generally comprise:
a. contacting a sample comprising a DNA molecule of interest (DMOI) with one or more forward primers and one or more reverse primers, wherein the or each of the forward primers is specific for a first region of interest, and the or each of the reverse primers is specific for a second, different, region of interest; and
b. conducting PCR.

In a first aspect, there is provided a method of detecting a genomic fusion event, comprising:
a. contacting a sample comprising DNA molecules of interest (DMOIs) with a pool of at least 20 region-specific forward primers and a pool of at least 20 region-specific reverse primers, wherein:
  i. each of the forward primers in the forward primer pool comprises a sequence specific for a first region of interest and a first primer binding site; and
  ii. each of the reverse primers in the reverse primer pool comprises a sequence specific for a second, different, region of interest and a second primer binding site;
b. amplifying the DMOIs using the region-specific primers;
c. conducting PCR using forward primers that target the first primer binding site and reverse primers that target the second primer binding site;
d. sequencing the PCR amplification product to provide a library of sequence reads, wherein the sequence reads comprise the sequence of a forward and/or reverse primer used in step (a);
e. using the sequence reads provided in step (d) to determine the sequence of the genomic fusion between the first and second regions of interest.

In some embodiments, the first primer binding site is the same in each of the at least 20 region-specific forward primers and the second primer binding site is the same in each of the at least 20 region-specific reverse primers. The first and second primer binding sites may be different from each other. The first and second primer binding sites act as universal primer bindings sites in a subsequent PCR.

Step (b) may comprise multiplex PCR, which is also a selective PCR, since an exponential amplification product will be produced in the presence of a genomic rearrangement event that brings the first and second regions into sufficient proximity to each other. Generally, the genomic rearrangement is a gene fusion.

The methods comprise sequencing the final amplification product. Hence in some embodiments the methods comprise decoding the genomic rearrangement (e.g. gene fusion) by sequencing. In some embodiments, the method comprises multiple PCR reactions, for example a first PCR using the region-specific primers and a second PCR using primers specific for sequences introduced into the amplicons by the primers used in a first PCR.

In a second aspect, there is provided a method, comprising:
a. providing a sample from a patient, said sample comprising one or more DMOIs; and
b. determining the presence or absence of a genomic rearrangement event according to a method disclosed herein.

The method may be a method of diagnosing or characterising cancer, a method of determining cancer prognosis, a method of determining cancer remission or relapse, a method of characterising cancer, a method of detecting progression of cancer, or a method of determining the presence or absence of residual cancer. The method may comprise extracting, isolating or enriching for the DMOI from the patient sample prior to determining the presence or absence of a genomic rearrangement. However, an advantage of the methods and kits disclosed herein is that enrichment of the sample for the DMOI is not required, and so the methods do not involve the loss of sensitivity due to inefficient enrichment methods.

In a third aspect there is provided a method of treating a disease, such as cancer, comprising
a. providing a sample from a patient, said sample comprising one or more cell-free DNA molecules of interest (DMOIs);
b. determining the presence or absence of a genomic rearrangement event according to a method disclosed herein; and
c. administering a therapy to the patient, such as a cancer therapy.

In a fourth aspect there is provided a method of determining a treatment regimen for a patient, such as a cancer patient or a patient suspected of having cancer, comprising:

a. providing a sample from a patient, said sample comprising one or more cell-free DNA molecules of interest (DMOIs);
b. determining the presence or absence of a genomic rearrangement event according to a method disclosed herein; and
c. selecting a treatment regimen for the patient according to the presence or absence of a genomic rearrangement in the one or more DMOIs.

The method may further comprise administering said treatment regimen to the patient.

In a fifth aspect there is provided a method of predicting a patient's responsiveness to a cancer treatment, comprising
a. providing a sample from a patient, said sample comprising one or more cell-free DNA molecules of interest (DMOIs);
b. determining the presence or absence of a genomic rearrangement event according to a method disclosed herein;
c. predicting a patient's responsiveness to a cancer treatment according to the presence or absence of a genomic rearrangement in the one or more DMOIs.

In another embodiment, there is provided a method of early cancer detection/diagnosis of cancer, comprising:
a. providing a sample from a patient, said sample comprising one or more cell-free DNA molecules of interest (DMOIs);
b. determining the presence or absence of a genomic rearrangement event according to a method disclosed herein;
c. diagnosing a patient as having cancer if a genomic rearrangement event is detected.

The methods disclosed herein are combined with sequencing of the amplification product of the forward and reverse primers to detect the genomic rearrangement.

The methods disclosed herein therefore comprise sequencing the amplification product and determining the sequence of the DNA that has been amplified (decoding the DMOI by sequencing). This enables non-specific (off-target) amplification to be discounted and true genomic rearrangements (such as gene fusions) to be identified and characterised. The methods allow the identification of a gene breakpoint in a gene fusion and enable a disease, in particular cancer, to be characterised. The methods can also be used to assess and/or monitor cancer progression in a subject, optionally a subject that has received or is receiving treatment for the cancer. The methods can also predict whether or not a patient will respond to a given cancer treatment.

In a further aspect there is provided a kit of parts comprising a plurality of forward primers and a plurality of reverse primers, wherein the forward primers are each specific for a first region of interest, and the reverse primers are each specific for a second, different, region of interest.

In a still further aspect there is provided a pool of forward and reverse primers, comprising a plurality of forward primers specific for a first region of interest and a plurality of reverse primers specific for a second region of interest, wherein the first and second regions of interest are different to each other. The kits and primer pools disclosed herein can be used in the methods disclosed herein to determine the presence or absence of a genomic rearrangement.

In a further embodiment there is provided a reaction mixture comprising:
a. a kit or pool of primers disclosed herein; and
b. a sample from a patient containing a DMOI derived from a neoplasm or a cancer.

In a further embodiment there is provided the kits or primer pools disclosed herein for use in the diagnosis of a disease such as cancer.

In a still further embodiment, there is provided a method for determining the presence or absence of a gene fusion in a DMOI, the method comprising:
a. providing the sequence of a DMOI as a sequence read;
b. identifying in the sequence read the presence of at least one forward primer binding site and the presence of at least one reverse primer binding site from a population of forward and reverse primers;
c. determine the corresponding genomic locations of the forward and reverse primer binding sites by reference to the sequences of the forward and reverse primer binding sites and the sequences downstream and adjacent to the forward and reverse primer binding sites in the sequence read:

determining the presence or absence of a gene fusion in the DMOI.

BRIEF DESCRIPTION OF THE FIGURES

The skilled artisan will understand that the drawings, described below, are for illustration purposes only. The drawings are not intended to limit the scope of the present teachings in any way.

FIG. 5: The sequence of the synthesised ROS1-CD74 fusion containing gblock is depicted. The gblock was fragmented to an average of 150 bp prior to inputting into the assay. SEQ ID NO: 5.

FIG. 6: Next Generation sequencing reads obtained from ROS1-CD74 gBlock. A. Two combinations of forward and reverse primers amplified the fusion gene (SEQ ID NOS: 5 and 6). B. The sequence of the read detected for each is shown. The sequence of the read is shown in bold letters within the geneblock sequence (SEQ ID NOS: 7 and 8).

DETAILED DESCRIPTION OF THE INVENTION

Figure 1:
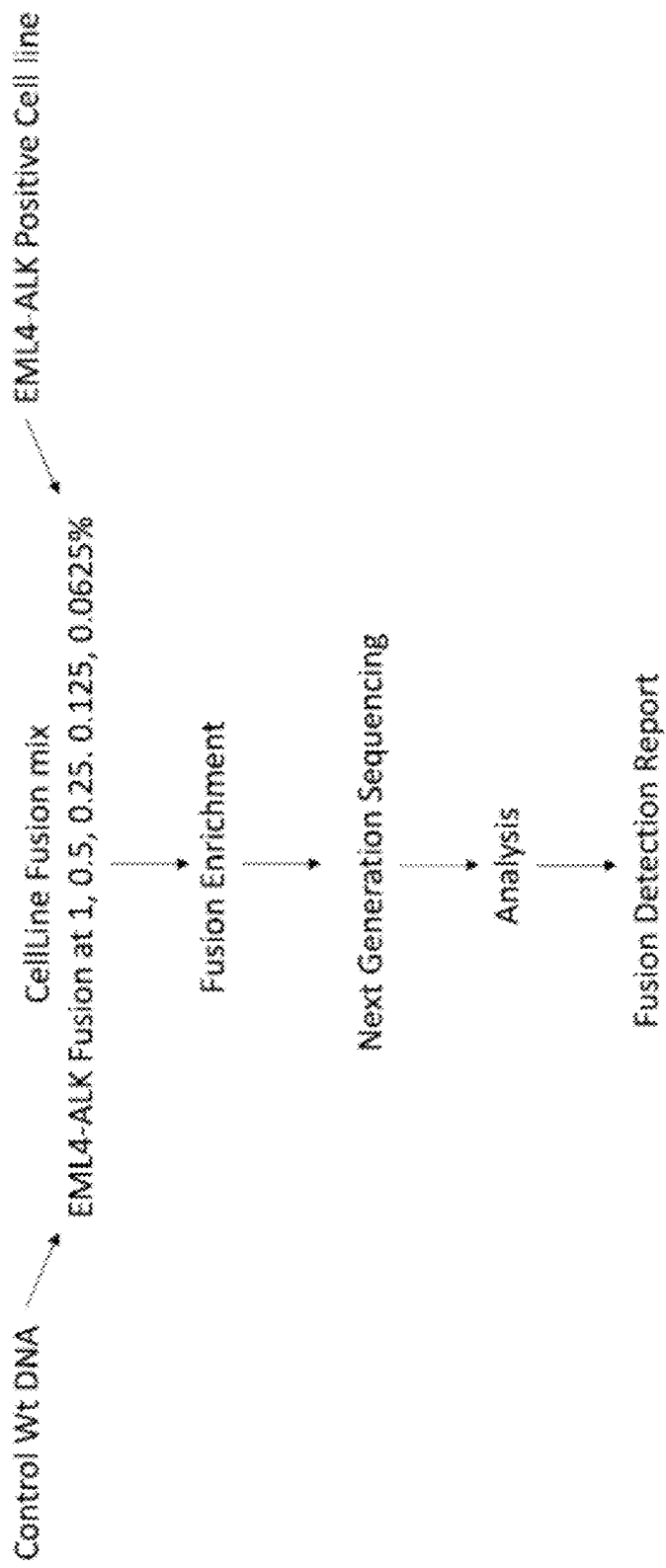
FIG. 1: Cell line fusion mix (custom product Horizon Discovery Group) consisting of a mixture of EML4-ALK fusion-positive DNA and normal (fusion-negative) DNA was serially diluted to achieve allelic fractions of 1%, 0.5%, 0.25%, 0.125% and 0.0625%. Fusion-negative human placental DNA (bioline) was added to maintain the genome input copy number constant at 4000 input copies. Fusion enrichment is achieved by selective PCR and a second PCR ensures the addition of barcoded illumina adapters. Fusion genes are decoded by next-generation sequencing e.g. on the NextSeq 500 Illumina platform. Sequencing data is screened for the presence of fusion genes using the described bioinformatic pipeline and data is published in a fusion detection report.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The present disclosure provides novel methods for detecting and determining the sequence of genomic rearrangements, in particular gene fusions, by using primers to target regions that are usually too far apart in a genome, chromosome or gene for an amplification product to be produced in a normal PCR. This is achieved by conducting a selective PCR comprising providing a forward primer (or preferably a pool of at least 20 forward primers) specific for a first region of interest and a reverse primer (or preferably a pool of at least 20 reverse primers) specific for a second region of interest, wherein the first and second regions of interest are different. In particular, the two regions of interest are located at distinct positions in a genome, chromosome or gene such that in a normal sample (i.e. a sample comprising DNA molecules in which a genomic rearrangement has not occurred) the two regions are too far apart for an amplification product to be produced in a normal PCR (for example, more than 1 kb apart or on different chromosomes). For example, the two regions could be two different genes. If a genomic rearrangement event occurs, such as a gene fusion event, it brings the two regions of interest into proximity with each other such that at least one pair of the forward and reverse primers are sufficiently close to each other to produce an amplification product in a PCR, even when the PCR only amplifies small DNA fragments (for example fragments up to 500 bp in length). The sequence of the amplification product is then determined to confirm the location of the primers used in the amplification reaction and therefore the presence and location of the genomic rearrangement in the sample. Multiple regions and multiple genomic rearrangements can be targeted in a single reaction. In preferred embodiments the primers are designed to target DNA sequences in the respective regions of interest that are not overlapping. Regions of interest can be large and span several kilobases, or even megabases, without impacting sequencing cost, as sequencing products will only be generated in a small number of cases (samples in which a genomic rearrangement has occurred, i.e. fusion-positive samples) as well as from a small region of the genome (where the fusion event occurred), no matter how large the regions of interest covered by the forward and reverse primers are.

The term "primer binding site" in the context of a forward primer or a reverse primer indicates that the forward primer or reverse primer 5' tail that is not specific for the region of interest and that, when copied, provides a sequence to which another primer can bind. Such a primer binding site is typically 8-30 nucleotides in length, although a primer binding site can be longer or shorter in some instances. Likewise, the site to which a forward or reverse primer binds is typically at least 8-30 contiguous nucleotides in length.

The term "primer binding site" can also be used in the context of the sequence read of the DMOI to denote the sequence to which the corresponding forward or reverse primer can bind. For example, in the context of analysis of the sequence reads, the forward and reverse primer binding sites refers to the region-specific sequence in the region-specific primers. The at least one forward primer binding site and the at least one reverse primer binding site could be the complement of the region-specific sequence from the corresponding forward or reverse region-specific primer or could have the same sequence as the region-specific sequence of a corresponding forward or reverse region-specific primer, depending on the direction of the sequence read. The skilled person is able to take such variations into account when conducting their analysis.

In any embodiments, all of the primers in a "pool of region-specific forward primers" can bind to the same strand, i.e., the top strand or the bottom strand, but not both strands, of a region of interest in a reference genome, where the term "reference genome", refers to a genome whose sequence is at least partially known. The sequences of several reference genomes, including the human genome, have been deposited at NCBI's GenBank database and other databases. A reference genome can be a "wild type" sequence. Likewise, all of the primers in a "pool of region-specific reverse primers" can bind also to the same strand, i.e., the top strand or the bottom strand, but not both strands, of a region of interest in the reference genome. The forward primers may bind to the same or different strand to the reverse primers.

The first region of interest and the second region of interest should be on different chromosomes or sufficiently distanced in the reference genome so that no amplification products are expected unless there is a rearrangement in which the first region of interest and the second region of interest become closely linked to one another. In some embodiments, the first and second regions of interest should be on different chromosomes in the reference genome, or distanced by at least 10 kb, at least 50 kb, or at least 100 kb if those regions are on the same chromosome in the reference genome. In embodiments in which cfDNA isolated from blood is analysed, the distance between the first and second regions of interest can be much shorter, e.g., at least 1 kb or at least 5 kb, because cfDNA is heavily fragmented (having a median size that is well below 1 kb, e.g., in the range of 50 bp to 500 bp) and, as such, no amplification products would be expected if the first and second regions are 1 kb or 5 kb apart.

In any embodiment, all of the forward primers in the forward primer pool may comprise: i. a sequence at the 3' end that is complementary to a binding site in a first region of interest and ii. a 5' tail that is not complementary to a sequence in the first region of interest, where the sequences at the 3' end of the forward primer are complementary to different sites in the first region of interest, and all of the reverse primers in the reverse primer pool may comprise: i. a sequence at the 3' end that is complementary to a binding site in the second region of interest and ii. a 5' tail that is not complementary to a sequence in the second region of interest, where the sequences at the 3' end of the reverse primer are complementary to different sites in the second region of interest.

In some embodiments, methods disclosed herein are used to exponentially amplify small stretches of DNA, for example DNA molecules that are up to 500 nucleotides in length. This be achieved in a number of ways. Usually, the DNA will be fragmented prior to carrying out the method. Fragmentation may have occurred already, for example in the body of a patient such that the sample obtained already contains fragmented DNA. Alternatively, a step of DNA fragmentation may be included in the method itself.

In one embodiment, there is provided a method of detecting a genomic rearrangement event, comprising:
 a. contacting a sample comprising a DNA molecule of interest (DMOI) with one or more forward primers and one or more reverse primers, wherein the or each of the forward primers is specific for a first region of interest, and the or each of the reverse primers is specific for a second, different, region of interest; and
 b. conducting PCR.

In one embodiment there is provided a method of detecting a genomic rearrangement event, comprising:
 a. contacting a sample comprising a DNA molecule of interest (DMOI) with a pool of forward primers specific for a first region of interest and a pool reverse primers specific for a second, different, region of interest;
 b. conducting PCR;
 c. determining the sequence of the amplification product of the PCR.

In a preferred embodiment, the method comprises all of the following steps:
 a. contacting a sample comprising DNA molecules of interest (DMOIs) with a pool of at least 20 region-specific forward primers and a pool of at least 20 region-specific reverse primers, wherein:
  i. each of the forward primers in the forward primer pool comprises a sequence specific for a first region of interest and a first primer binding site; and
  ii. each of the reverse primers in the reverse primer pool comprises a sequence specific for a second, different, region of interest and a second primer binding site;
 b. amplifying the DMOIs using the region-specific primers;
 c. conducting PCR using forward primers that target the first primer binding site and reverse primers that target the second primer binding site;
 d. sequencing the PCR amplification product to provide a library of sequence reads, wherein the sequence reads comprise the sequence of a forward and/or reverse primer used in step (a);
 e. using the sequence reads provided in step (d) to determine the sequence of a genomic fusion between the first and second regions of interest.

In some embodiments, the first primer binding site is the same in each of the at least 20 region-specific forward primers and the second primer binding site is the same in each of the at least 20 region-specific reverse primers. The first and second primer binding sites may be different from each other. The first and second primer binding sites may also be universal primer bindings sites.

The combination of the selective PCR with the step of sequencing allows non-specific and off-target amplification products to be ruled out and genuine genomic rearrangement events to be identified.

The genomic rearrangement event can be an unknown genomic rearrangement event, since no prior knowledge of the exact nature of the genomic rearrangement is needed for the methods disclosed herein to be able to detect and characterise the genomic rearrangement.

The first and second regions of interest may be in different genes. The different regions of interest or different genes are located at different places in a given genome when a genomic rearrangement has not occurred, and may even be located on different chromosomes when a genomic rearrangement event has not occurred.

The forward primers and reverse primers are present in a pool of forward and reverse primers. The forward primers in the pool of forward primers are specific to a first region of interest (such as a first gene), and the reverse primers in the pool of reverse primers are specific to a second, different, region of interest (such as a second gene). Given the normal location of the first and second regions or first and second genes, when PCR is conducted, a PCR product is produced when a genomic rearrangement event has occurred. Therefore, the PCR can be referred to as a selective PCR.

In some embodiments, the first and second regions of interest are located on the same chromosome but are located such that no PCR amplification product is generated in the absence of a genomic rearrangement event. In some embodiments, the first and second regions of interest are located on the same chromosome but are separated by a number of base pairs that prevents a PCR occurring under normal conditions. For example, the first and second regions may be at least 100 base pairs, or at least 250 base pairs, or at least 500 base pairs, preferably at least about 1000 base pairs apart.

In some embodiments, each of the first and second region of interest are at least 1 kilobase in length and the first and second regions are separated by at least 1 kilobase when no genomic rearrangement event has occurred.

Given that the sequence of an amplification product is indicative of genomic rearrangement event, the methods disclosed herein comprise determining the sequence of a PCR amplification product. In particular, the relevant PCR amplification product to detect is the amplification product resulting from the PCR of one or more pairs of forward and reverse primers targeting the two regions of interest. Determining the sequence of a PCR amplification product allows the definitive detection of genomic rearrangements as non-specific or off-target amplification can be discounted. Therefore, it is the sequence of the DMOI that is indicative of the presence of a genomic rearrangement event between the first and second region of interest.

As noted above, the forward and reverse primers are present in pools of primers. In such embodiments, the primers preferably tile the regions of interest. The forward primers tile the first region of interest and the reverse primers tile the second region of interest. Tiling the regions involves providing primers that target different stretches of DNA in the respective regions of interest. Primers in the same pool of forward or reverse primers target different stretches of DNA in the respective regions of interest.

In a preferred embodiment, the DNA sequences in the regions of interest that are targeted by the pool of forward or reverse primers do not overlap. In other words, the region-specific tract of each member of a primer pool is different and does not overlap with the region-specific tract of any other member of the primer pool. However, in a given pool multiple copies of the same primer are of course possible, and indeed are preferred. In some embodiments, the pool of primers (either forward or reverse) comprises a set of primers each targeting a different, non-overlapping, DNA tract of the region of interest, but the pool comprises multiple copies of each member of the set.

As noted above, when a pool of primers tile a region of interest, the tiling is such that the primers do not target overlapping DNA stretches of the region of interest, and more preferably the primers tile at intervals, with gaps between the stretches of DNA in the region of interest being targeted by the primers. In some embodiments, the forward and/or reverse primers tile the first and/or second region of interest at intervals of from about 10 to about 2000 base pairs, from about 10 to about 1000 base pairs, from about 10 to about 500 base pairs, from about 10 to about 250 base pairs, from about 10 to about 150 base pairs, from about 25 to about 125 base pairs, from about 50 to about 100 base pairs, or from about 60 to about 90 base pairs. An appropriate frequency for tiling the regions of interest at certain intervals can be determined by the skilled person. However, tiling at intervals of from about 60 to about 90 base pairs (or up to about 100 base pairs) can be particularly useful for targeting DNA that is approximately 150-160 base pairs in length, such as circulating tumour DNA.

Similarly, the size of the gaps between sequences of the regions of interest targeted by the primers in a primer pool may be from 1 to 150 bases, from 10 to 100 bases, from 25 to 100 bases or preferably from 50 to 100 bases. Such intervals are particularly useful for ctDNA, which are approximately 160 base pairs in length. Hence intervals of 50 to 100 bases (e.g. 75 bases) helps to ensure that a ctDNA derived from a region of interest will be targeted by at least one of the forward or reverse primers in the pool.

In some embodiments the pool of forward primers comprises at least 20, at least 50 or at least 100 different forward primers. Preferably the different primers target stretches of DNA in the region of interest that are not overlapping with each other. Multiple copies of each primer may be present in the pool.

In some embodiments, the pool of reverse primers, wherein the pool of reverse primers comprises at least 20, at least 50 or at least 100 different reverse primers. Preferably the different primers target stretches of DNA in the region of interest that are not overlapping with each other. Multiple copies of each primer may be present in the pool.

In one embodiment, the method comprises contacting a sample containing the DMOI with a pool of forward and a pool of reverse primers, wherein the pool of forward primers comprises at least 20, at least 50 or at least 100 different forward primers and a pool of reverse primers comprising at least 20, at least 50 or at least 100 different reverse primers. Preferably the different primers target stretches of DNA in the region of interest that are not overlapping. Multiple copies of each primer may be present in the pool.

Preferably at least 100 forward and reverse primers are used, although the total number could be higher (for example at least 500 or at least 1000 forward and reverse primers) to enable larger and more regions of interest to be targeted in a single reaction.

The pool of forward primers may comprise at least 20 different forward primers and the pool of reverse primers may comprise at least 20 different reverse primers.

In some embodiments, the methods comprise contacting a sample comprising a DMOI with a pool of at least 20 different forward primers (for example at least 100 different forward primers) specific for a first region of interest and a pool of at least 20 different reverse primers (for example at least 100 different reverse primers) specific for a second region of interest, wherein each of the first and second region of interest are at least 1 kilobase in length and the first and second regions are separated by at least 1 kilobase when no genomic rearrangement event has occurred, and further wherein the primers tile their respective regions of interest at intervals of from 50 to 100 bases. The first and second regions may be different genes.

The primers may be of any suitable length, for example they may be from 5 to 50 base pairs in length, for example from 10 to 40 base pairs in length, or from 18 to 35 base pairs in length. The skilled person is familiar with the use of primers in PCR and would be able to determine appropriate size of a primer.

To assist in the analysis, the sequences of all the PCR primers used to target the first and second regions of interest (the selective PCR primers) are known.

The methods disclosed herein are useful for detecting the sequence of multiple types of genomic rearrangement events. Of particular significance are gene fusion events, which may be associated with a disease or condition. In some embodiments, the method comprises determining the presence or absence of a genomic rearrangement that is known or is suspected to be associated with a disease or disorder. In some embodiments, the methods determine the presence or absence of a gene fusion event that is known, or is suspect to be, associated with cancer. One advantage of the methods and kits disclosed herein is that they can detect any gene fusion even between two genes, without the need for prior knowledge of the precise fusion event that has occurred. The methods and kits disclosed herein can also significantly reduce the amount of sequencing required since the gene rearrangement is selectively enriched. The step of sequencing the amplification product provides information on the precise fusion or genomic rearrangement event that has occurred and ensures that only a true gene rearrangement is detected/reported.

When a genomic rearrangement event has occurred, at least one pair of forward and reverse primers anneals to the DMOI within 500 base pairs from each other, or within 400 base pairs from each other, or within 300 base pairs from each other, or within 200 base pairs from each other, or within 175 base pairs from each other.

The primers themselves may be gene specific primers, with each of the forward primers being specific for a first gene (i.e. a first region of interest) and each of the reverse primers being specific for a second, different, gene (i.e. a second region of interest). The primers comprise a region-specific sequence that enables the primer to anneal to a region of interest.

The primers used in the selective PCR may also comprise other features. For example, the primers may comprise sequencing adaptors or partial sequencing adaptors that allow the amplification product (if one is produced) to be sequenced without the need for ligating on adaptors separately (see, for example, Weaver et al., Nat Genet., 2014; 46: 837-843 and Forshew et al., Sci Transl Med., 2012; 4). Adaptors are moieties that allow sequencing of DNA, in particular using high-throughput sequencing (i.e. next generation sequencing, NGS), and they are familiar to the skilled person. Most commonly, and potentially in addition to sequencing adaptors, the region-specific primers may comprise one or more primer binding sites, in particular universal primer binding sites (UPS). The incorporation of the UPSs into the amplification product allows the amplification product of a first reaction to be targeted again with a further pair of primers that are specific for the UPS. The primers used in the second PCR may themselves comprise the sequencing adaptors or partial sequencing adaptors that allow the amplification product of the second PCR to be sequenced using NGS. When two or more PCR reactions are used, the methods may comprise a step of purification of the amplicons from the first PCR before conducting the second PCR. The first PCR is a multiplex PCR, whereas the second PCR is not multiplex PCR, since only primers specific for the universal primer sites introduced in the first round of PCR are used in the second PCR. However, this second PCR step may still act to selectively amplify DMOIs that represent genomic rearrangement events, since only those DMOIs will have been amplified in the first PCR (apart from some possible non-specific PCR amplification), although in itself this is not a selective amplification step.

PCR can be used to introduce a number of features into the DMOI. For example, PCR may incorporate a universal primer binding site (or sequencing adapter, as discussed above), a molecular barcode and/or index sequence into the PCR product. Index sequences may be a sequence that identifies the DNA as deriving from a particular sample or patient, and so may be a patient or sample-specific index sequence. A molecular barcode may be used to identify different starting DMOI in a given sample, and so may be DMOI-specific molecular barcodes. Typically, a molecular barcode and universal primer binding sites may be introduced in the first PCR using the region-specific primers. An index sequence may typically be incorporated in a second PCR using primers that target the universal primer binding sites introduced in the first PCR.

Figure 7:
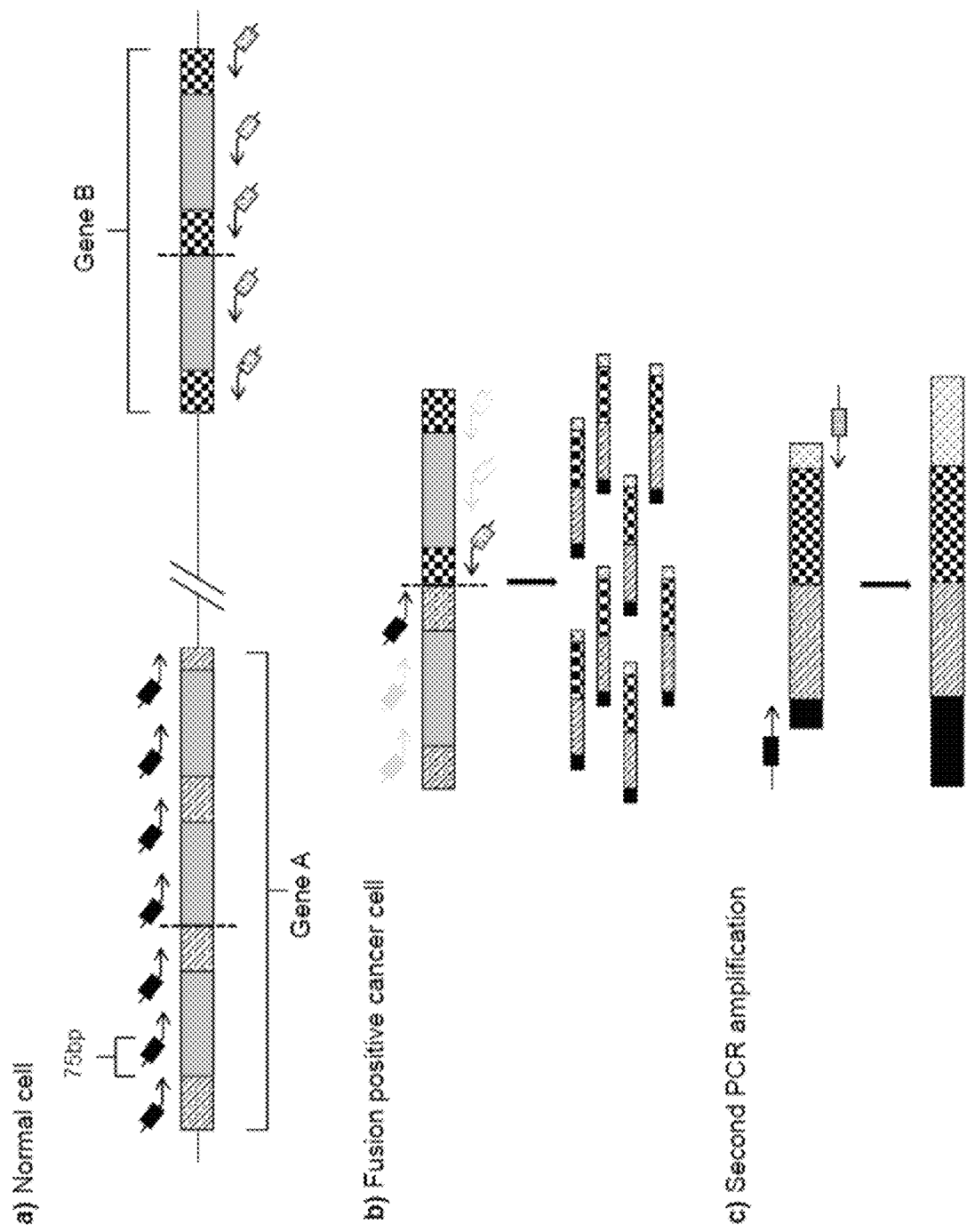
FIG. 7: Example 2-step workflow showing multiplex PCR conducted with primers that tile genes of interest at intervals (75 bp in this example). Gene A is tiled only with forward primers and Gene B is tiled only with reverse primers. The primers contain a universal primer site (UPS) (for example part of an Illumina adaptor sequence) at the 5' end and a gene specific sequence at the 3' end. A. in normal cells that do not have a gene fusion, PCR amplification does not occur as the distance between the genes is too great. B. in fusion-positive cancer cells, Genes A and B are brought into close proximity with one another (for example within 150 bp) so a product is generated by PCR amplification C. The presence of the UPSs (such as UPSs incorporated in partial sequencing adaptors, such as partial Illumina adaptors) allows the construction of complete sequencing adaptors (such as Illumina adaptors) in a second round of PCR. This second round of PCR uses primers that anneal to the UPS element of the original primers (at the 3' end of the primer) and contain the rest of the sequencing adaptor (at the 5' end of the primer).

Sequencing adaptors may be incorporated in the first or second PCR. Alternatively, partial sequencing adaptors may be incorporated into the first PCR and partial sequencing adaptors may be incorporated in a second PCR, subsequently completing the sequencing adaptors. The universal primer binding sites that are incorporated in the method may make up a first portion of a sequencing adaptor that is completed with a second portion of the sequencing adaptor when a subsequent PCR takes place. Therefore, the sequencing adaptors may comprise the universal primer binding sites. Such an embodiment is described in FIG. 7. However, the precise method used to incorporate the sequencing adaptors is not crucial and the incorporation of sequencing adaptors to allow the amplification product to be sequenced is familiar to the skilled person and appropriate PCR based methods may be used. Preferably the sequencing adaptors are not incorporated or attached by ligation.

The step of "amplifying the DMOIs using the region-specific primers" may be achieved in a number of ways. A key aspect is to incorporate the first and second universal primer binding sites from the region-specific primers into a reaction product to allow a subsequent PCR targeting those first and second primer binding sites.

For example, amplification of the DMOIs using the region-specific primers may comprise extension reactions (as in the sequential methods, discussed below) and/or PCR. There are therefore several appropriate workflows for the methods disclosed herein. In some embodiments, the sample comprising the DMOIs is contacted with the forward and reverse region-specific primers and PCR conducted with forward and reverse primers present. The PCR incorporates universal primer binding sites into the PCR product, which is then targeted in a second PCR using universal primers to incorporate sequencing adaptors. For example, as follows:

a. contacting a sample comprising DNA molecules of interest (DMOIs) with a pool of at least 20 region-specific forward primers and a pool of at least 20 region-specific reverse primers, wherein:
  i. each of the forward primers in the forward primer pool comprises a sequence specific for a first region of interest and a first primer binding site; and
  ii. each of the reverse primers in the reverse primer pool comprises a sequence specific for a second, different, region of interest and a second primer binding site;
b. amplifying the DMOIs using the region-specific primers by PCR to incorporate the first and second primer binding sites into the amplification product;
c. conducting a further PCR using forward primers that target the first primer binding site and reverse primers that target the second primer binding site to incorporate sequencing adaptors into the amplification product;
d. sequencing the PCR amplification product to provide a library of sequence reads, wherein the sequence reads comprise the sequence of a forward and/or reverse primer used in step (a);
e. using the sequence reads provided in step (d) to determine the sequence of a genomic fusion between the first and second regions of interest.

In some embodiments, the first primer binding site is the same in each of the at least 20 region-specific forward primers and the second primer binding site is the same in each of the at least 20 region-specific reverse primers. The first and second primer binding sites may be different from each other. The first and second primer binding sites may also be universal primer bindings sites.

It is possible to even conduct the entire method using a single PCR, in which the incorporation of universal primer binding sites is not required, for example as follows:

a. contacting a sample comprising DNA molecules of interest (DMOIs) with a pool of at least 20 region-specific forward primers and a pool of at least 20 region-specific reverse primers, wherein:
  i. each of the forward primers in the forward primer pool comprises a sequence specific for a first region of interest and a first primer binding site and a sequencing adaptor; and
  ii. each of the reverse primers in the reverse primer pool comprises a sequence specific for a second, different, region of interest and a second primer binding site, and a sequencing adaptor;
b. amplifying by PCR the DMOIs using the region-specific primers, wherein the sequencing adaptors are incorporated into the amplification product by the PCR;
c. sequencing the PCR amplification product to provide a library of sequence reads, wherein the sequence reads comprise the sequence of a forward and/or reverse primer used in step (a);
d. using the sequence reads provided in step (d) to determine the sequence of the genomic fusion between the first and second regions of interest.

In some embodiments, the first primer binding site is the same in each of the at least 20 region-specific forward primers and the second primer binding site is the same in each of the at least 20 region-specific reverse primers. The first and second primer binding sites may be different from each other. The first and second primer binding sites may also be universal primer binding sites. The forward and reverse primers may also comprise a molecular barcode and/or an index sequence.

Alternatively, the method can be conducted sequentially, which requires the use of one or more extension reactions followed by one or more PCR amplifications. For example, the sample comprising the DMOIs may be contacted with the forward region-specific primers, and one or more extension reactions conducted to extend the annealed primers along the DMOI. The forward primers comprise a region-specific sequence and a first primer binding sequence for use in a subsequent PCR. The one or more extension reactions incorporate the first primer binding site into the daughter molecules and also amplifies a first strand of the DMOI. Subsequently, one or more extension reactions are conducted using the reverse region-specific primers to incorporate a second primer binding site into the daughter molecules and also amplify the second strand of the DMOI. A PCR can then be conducted using primers that target the first and second primer binding sites incorporated by the one or more extension reactions. That PCR may also incorporate sequencing adaptors to allow the reaction product to be sequenced and the genomic rearrangement to be characterised. Note that the method may comprise conducting a single extension reaction for the forward primer and/or a single extension reaction for the reverse primer. However, in preferred embodiments, the method comprises a plurality of extension reactions for both the forward and reverse primers. Conducting a plurality of extension reactions means:

a) contacting the DMOIs with the forward region-specific primers;
b) allowing the forward region-specific primers to anneal to the DMOIs;
c) conducting an extension reaction to extend annealed forward region-specific primers along the DMOI;
d) denaturing the resulting double-stranded DNA molecule; and
e) repeating steps (b) to (d) a plurality of times.

The same steps can be undertaken for the reverse region-specific primers.

The skilled person will be aware of suitable reaction conditions to allow the components of the reaction to anneal, extend or denature, as appropriate.

Accordingly, in one embodiment, the method comprises:
a. contacting the sample comprising the DMOIs with the pool of at least 20 region-specific forward primers;
b. conducting one or more extension reactions to extend annealed forward primers along the DMOIs and to introduce the first primer binding site into the extension product;
c. optionally removing or deactivating the region-specific forward primers from the reaction mixture;
d. contacting a sample obtained in step (c) with the pool of at least 20 region-specific reverse primers;
e. conducting one or more extension reactions to extend annealed reverse primers along the DMOIs and to introduce the second primer binding site into the extension product;
f. optionally removing or deactivating the region-specific reverse primers from the reaction mixture; and
g. conducting PCR using forward primers that target the first priming binding site introduced in step (b) and reverse primers that target the second priming binding site introduced in step (e) to amplify a genomic fusion event between the first and second regions of interest.

The forward primers used in step (a) comprise a sequence specific for a first region of interest and a first primer binding site, and in some embodiments the first primer binding site is the same in each of the forward primers in the forward primer pool. The reverse primers used in step (d) comprise a sequence specific for a second, different, region of interest and a second primer binding site, and in some embodiments the second primer binding site is the same in each of the forward primers in the reverse primer pool.

The one or more extension reactions of steps (b) and (e) incorporate the first and second primer sites present in the forward and reverse region-specific primers into the extension products. The first and second primer sites introduced in steps (b) and (e) therefore act as a forward and reverse primer sites for the primer pair used in step (g) to amplify a genomic rearrangement between the first and second regions of interest. A fusion specific exponential reaction product will only be produced when a genomic rearrangement has occurred to situate the first and second primers sites sufficiently close together in a single molecule, hence allowing a genomic rearrangement between the first and second regions to be identified.

In any methods disclosed herein that comprise the incorporation of first and second universal primer binding sites into the amplification product, the first and second universal primer binding sites are different from each other.

It is also noted that the use of "forward" and "reverse" as used throughout is simply for the purposes of orientation and explanation. The skilled person will be aware that the "forward" and "reverse" designation could be switched, without affecting the method in any way.

In another embodiment, the method may comprise:
a. contacting the sample comprising the DMOIs with the pool of at least 20 forward primers;
b. conducting one or more extension reactions to extend annealed forward primers along the DMOIs and to introduce the first primer binding site into the extension product;
c. optionally removing or deactivating the forward primers from the reaction mixture;
d. contacting a sample obtained in step (c) with:
  i. the pool of at least 20 reverse primers; and
  ii. primers targeting the first primer binding site added in step (a); and
e. conducting PCR to amplify a genomic fusion event between the first and second regions of interest.

Again, the forward primers used in step (a) comprise a sequence specific for a first region of interest and a first primer binding site, and in some embodiments the first primer binding site is the same in each of the forward primers in the forward primer pool. The reverse primers used in step (d)(i) comprise a sequence specific for a second, different, region of interest and a second primer binding site, and in some embodiments the second primer binding site is the same in each of the reverse primers in the reverse primer pool.

Similarly, the one or more extension reactions of step (b) incorporates the first primer site into extension products arising from DMOIs that comprise the first region of interest. In step (d), fusion-specific exponential PCR will occur where the second region of interest is sufficiently close to the first priming site introduced in the one or more extension reactions of step (b). The first primer site introduced in step (b) and the second region of interest targeting in step (d)(i) therefore act as a forward and reverse primer sites for the primer pair used in step (e) to amplify a genomic rearrangement between the first and second regions of interest.

In the two sequential methods described above using one or more extension reactions, it is still possible to use primer pools that target multiple first and second regions of interest, including using panels of primers that tile the regions of interest. Also, the priming sites incorporated into the extension and/or PCR products can be universal primer binding sites.

Methods of removal or deactivation of primers are well known to persons of skill in the art. For example, the step of removing the primers may comprise removal by size selection, size exclusion columns, gel extraction, or silica membrane columns. The step of deactivating the primers may comprise enzymatic digestion of the primers. The steps of removal and/or deactivation of primers are optional. However, they may be present in preferred embodiments.

In both example sequential methods outlined above, the method further comprises a step of sequencing the PCR product. This may be achieved by conducting a further PCR amplification reaction, for example to introduce sequencing adaptors into the DMOI, prior to sequencing the DMOIs. The sequencing adaptors allow the amplified DMOIs to be sequenced using next generation sequencing techniques. Alternatively, the DMOIs can be prepared for sequencing using a single PCR by using primers that incorporate sequencing adaptors into the DMOIs during the first PCR. This can be achieved by, for example, using primers in the first PCR that also incorporate the sequencing adaptors, avoiding the need for an additional PCR.

In one embodiment, the method comprises
a. contacting the sample comprising the DMOIs with the pool of at least 20 forward primers;
b. conducting one or more extension reactions to extend annealed forward primers along the DMOIs and to introduce the first primer binding site into the extension product;
c. optionally removing or deactivating the forward primers from the reaction mixture;
d. contacting a sample obtained in step (c) with the pool of at least 20 reverse primers;

e. conducting one or more extension reactions to extend annealed reverse primers along the DMOIs and to introduce the second primer binding site into the extension product;
f. optionally removing or deactivating the reverse primers from the reaction mixture; and
g. conducting PCR using forward primers that target the first priming binding site introduced in step (b) and reverse primers that target the second priming binding site introduced in step (e) to amplify a genomic fusion event between the first and second regions of interest, wherein either:
 i. the primers used in step (g) comprise sequencing adaptors; or
 ii. the method further comprises a second PCR amplification reaction to incorporate sequencing adaptors into the reaction product; and
h. sequencing the reaction product of step (g).

In another embodiment the method comprises:
a. contacting the sample comprising the DMOIs with the pool of at least 20 forward primers;
b. conducting one or more extension reactions to extend annealed forward primers along the DMOIs and to introduce the first primer binding site into the extension product;
c. optionally removing or deactivating the forward primers from the reaction mixture;
d. contacting a sample obtained in step (c) with:
 i. the pool of at least 20 reverse primers; and
 ii. primers targeting the first primer binding site added in step (a); and
e. conducting PCR to amplify a genomic fusion event between the first and second regions of interest, wherein either:
 i. the primers used in step (d) comprise sequencing adaptors; or
 ii. the method further comprises a second PCR amplification reaction to incorporate sequencing adaptors; and
f. sequencing the reaction product of step (e).

As noted, the methods disclosed herein comprise sequencing the amplification product from a PCR (either the first PCR, or a second or subsequent PCR if a second or subsequent PCR is used). Hence in some embodiments, the step of determining the presence or absence of a genomic rearrangement event comprises determining the sequence of the DMOI (or rather, the amplification product, which corresponds to the portion of the DMOI that has been amplified). The sequencing can be high-throughput sequencing (next generation sequencing). In some embodiments, the high-throughput sequencing is selected from the group consisting of sequence-by-synthesis (SBS), sequencing-by-ligation (SBL) and long-read sequencing (LRS). In some embodiments, the sequencing-by-synthesis is selected from the group consisting of cyclic reversible termination SBS and single-nucleotide addition SBS. In some embodiments, the long-read sequencing is selected from the group consisting of single-molecule LRS and synthetic long-read LRS. Specific methods include platforms such as Illumina (e.g. Mi-Seq or Hi-Seq), Oxford Nanopore, Pacific Biosciences, Roche 454, Ion torrent (Proton/PGM sequencing), SOLiD sequencing etc.

Prior to sequencing of the amplicons generated from the various PCR reactions used in the methods, the methods may comprise a step of purification of the amplicons. Methods for purification are known to the skilled person and commercial kits are available for this purpose (for example SPRISelect from Beckman Coulter). The same techniques can be used to purify the amplicons between PCR reactions.

Other steps that may be undertaken prior to sequencing may include size selection. For example, the methods may comprise a step of selecting amplicons having a size of between 100 and 500 base pairs (for example between 200 and 350 base pairs). Alternatively, or additionally, the amplicons may also be quantified prior to sequencing.

Some embodiments also provide a method for determining the sequence of a DNA molecule of interest (DMOI) or a portion thereof (said portion comprising a junction of the genomic rearrangement or the junction of a gene fusion), the method comprising:
a. providing a sample obtained from a patient, wherein the sample comprises a DMOI;
b. optionally processing the sample;
c. conducting a first PCR using a pool of at least 20 forward and a pool of at least 20 reverse primers disclosed herein, wherein the first PCR incorporates universal primer binding sites;
d. conducting a second PCR using at least one pair of forward and reverse primers that are specific for the universal primer binding sites incorporated in the first PCR, wherein the second PCR incorporates sequencing adaptors into the amplification product of the PCR; and
e. determining the sequence of the DMOI or portion thereof.

The disclosure also provides a method for determining the sequence of a DNA molecule of interest (DMOI) or a portion thereof (said portion comprising a junction of the genomic rearrangement or the junction of a gene fusion), the method comprising:
a. providing an amplicon prepared by a method disclosed herein (such as method steps (a) to (d) above or any method of detecting genomic fusions disclosed herein); and
b. determining the sequence of the DMOI or portion thereof.

The above methods can be used to characterise the genomic rearrangement or gene fusion by determining its sequence.

Determining the sequence of the tagged and enriched DMOI can be carried out according to any suitable method known to the skilled person. However, given the benefits of such approaches, next-generation sequencing (NGS) methods are preferred. Next-generation sequencing is also referred to as high-throughput sequencing and massively-parallel sequencing in the art and is known and understood by the skilled person. A review of next-generation sequencing techniques is provided in Goodwin et al., "Coming of age: ten years of next-generation sequence technologies", 2016, *Nature Reviews,* 17:333-351.

Methods disclosed herein may comprise paired-end sequencing, so as to provide the complete sequence of the DMOI in the sequence read, even if the sequence read length is shorter than the length of the DMOIs. Paired-end sequence reads are known to the skilled person. Preferably, the sequence reads include the sequence of both the forward and reverse region-specific primers used in the selective amplification step. Since the sequencing adaptors are incorporated using primers that incorporate the sequencing adaptors upstream (i.e. 5') of the forward and reverse region-specific primers (in particular upstream of the first and second universal primer binding sites incorporated in the first amplification step), it will always be possible to provide sequence reads that comprise the sequence of the forward and reverse region-specific primers (or, at the very least, the component of the forward and reverse region-specific primers that anneals to the first or second region of interest, respectively).

In some embodiments comprising NGS, the method may further comprise localising amplified DMOIs to discrete sites. The discrete sites may comprise a solid or semi-solid substrate. The method may also comprise hybridising or immobilising the DMOIs to the solid or semi-solid substrate and clonally amplifying the localised DMOIs.

In one embodiment, there is provided a method comprising:
  a. contacting a sample comprising a DNA molecule of interest (DMOI) with a pool of primers comprising at least 20 forward primers and at least 20 reverse primers, wherein the forward primers are specific for a first region of interest and the reverse primers are specific for a second, different, region of interest, and wherein the primers comprise a region-specific sequence and a sequencing adaptor;
  b. conducting PCR; and
  c. sequencing the amplification product or products of the PCR using high-throughput sequencing.

It is also possible to use multiple pools of primers. For example, in one embodiment, there is provided a method comprising:
  a. contacting a sample comprising a DNA molecule of interest (DMOI) with at least two pools of primers, wherein each pool of primers comprises a set of at least 20 forward primers and at least 20 reverse primers, wherein each set of forward primers are specific for a first region of interest and each set of reverse primers are specific for a second, different, region of interest, and wherein the primers comprise a region-specific sequence and a sequencing adaptor;
  b. conducting PCR; and
  c. sequencing the amplification product or products of the PCR using high-throughput sequencing.

In one embodiment, there is provided a method comprising:
  a. contacting a sample comprising a DNA molecule of interest (DMOI) with a pool of primers comprising at least 20 forward primers and at least 20 reverse primers, wherein forward primers are specific for a first region of interest and the reverse primers are specific for a second, different, region of interest, and wherein the primers comprise a region-specific sequence and a universal primer binding site;
  b. conducting PCR;
  c. contacting the amplification product from step (b) with one or more sets of forward and reverse primers that are specific for the universal primer binding sites introduced by the first PCR, wherein the primers comprise sequencing adaptors;
  d. conducting a second PCR; and
  e. sequencing the amplification product or products of the PCR using high-throughput sequencing.

In one embodiment, there is provided a method comprising:
  a. contacting a DNA molecule of interest (DMOI) with at least two pools of primers, wherein each pool of primers comprises a set of at least 20 forward primers a set of at least 20 reverse primers, wherein each set of forward primers are specific for a first region of interest and each set of reverse primers are specific for a second, different, region of interest, and wherein the primers comprise a region-specific sequence and a universal primer binding site;
  b. conducting PCR;
  c. contacting the amplification product from step b. with one or more sets of forward and reverse primers that are specific for the universal primer binding sites introduced by the first PCR, wherein the primers comprise sequencing adaptors;
  d. conducting a second PCR; and
  e. sequencing the DMOI using high-throughput sequencing.

In some embodiments it is advantageous to include a positive control. This is to ensure the assay has been carried out correctly to avoid false negative results. For example, the method may comprise including one or more pairs of primers that are specific to a genetic alteration that is different to the genomic rearrangement targeted by the pool of forward and reverse primers. For example, the "genetic alteration" may be a single nucleotide polymorphism (SNP), INDEL, single nucleotide variants (mutations), substitutions, duplications, insertions, deletions, gene copy number variations, and structural variants, including inversions and translocations, or another genetic alteration of interest. The additional primer pair or primer pairs target a region known to contain the genetic alteration of interest. The "genetic alteration" targeted by the "control primers" is distinct from the "genomic rearrangement event" targeted by the "genomic rearrangement primers".

Additionally, the use of one or more pairs of primers that are specific to a genetic alteration that is different to the genomic rearrangement targeted by the pool of forward and reverse primers may allow further characterisation of, for example, the cancer being diagnosed using the assay. For example, the method could be combined with primers that are selective for specific cancer mutations, such as point mutations. Such embodiments would not include the additional primers only as positive controls but also to provide additional information about the nature of the cancer.

If the method comprises one PCR (for example when the region-specific primers already include sequencing adaptors for sequencing the amplification products), the additional primer pair or primer pairs targeting a different genetic alteration are generally included in the first reaction mixture such that a single PCR can amplify the genomic rearrangement DMOI (if present) and the additional genetic alteration. If the method comprises two PCR reactions (for example when the forward and reverse region-specific primers include UPSs, and a second PCR introduces the sequencing adaptors into the amplification product from the second PCR), the additional primer pair or primer pairs targeting a different genetic alteration may be included in either the first PCR mixture or the second PCR mixture, but preferably will be included in the first PCR mixture.

The control primer pair(s) target the same region of interest. Hence they are different to the forward and reverse primers that target different regions of interest. As such, an amplification product should occur from the control primer pair(s) regardless of the presence or absence of a genomic rearrangement event. It is also possible that one member of the control primer pair or pairs is contained within the pool of forward or reverse primers targeting the genomic rearrangement event. Hence the region containing the genetic alteration may be within or may overlap or overlay with the first or second region of interest targeted by the forward and reverse tiling primers. In other embodiments, the control primer pair(s) target a region or gene that is different to the regions or genes targeted by the genomic rearrangement primers.

To take into account the need to detect an amplification product arising from a genomic rearrangement event as being distinct from an amplification product arising from a genetic alteration, the genomic rearrangement primers may be present at a higher concentration than the control primers. For example, each of the control primers may be present at a concentration that is 50% or lower than that of the genomic rearrangement primers.

Multiple "control" primer pairs can be included in the same reaction, with each primer pair targeting a different genetic alteration. For example, the set of control primers may comprise up to 5, up to 10 or up to 20 or more primer pairs, each primer pair targeting a different genetic alteration. Of course, multiple copies of each primer pair will generally be added to the reaction mixture to ensure the PCR takes place correctly.

As with the selective PCR, the control primer pairs may incorporate adaptor sequences (also referred to herein as sequencing adaptors) into the amplicon from the control PCR. Alternatively, the control primer pairs may incorporate universal primer binding sites into the amplicons from the control PCR, and these are targeted using a further PCR using primers specific for the universal primer binding sites and themselves incorporating the sequencing adaptors.

In embodiments comprising the use of control primers, the method may include detecting the presence or absence of the genetic alteration. This may comprise sequencing a PCR amplification product.

In one embodiment, the methods comprise:
a. providing a sample comprising a DMOI;
b. optionally extracting the DMOI from the sample;
c. conducting a selective PCR on the sample (or extracted DMOI) using a pool of at least 20 forward primers specific for a first gene and a pool of at least 20 reverse primers specific for a second gene, wherein the pool of forward primers tiles the first gene (or a region thereof) and the pool of reverse primers tile the second gene (or a region thereof), with space of between 50 and 100 nucleotide bases between adjacent primers in the pools, wherein the selective PCR is performed concurrently with a control PCR using one or more primer pairs specific to a genetic alteration (such as a SNP), and further wherein the selective and control PCR reactions incorporate universal primer binding sites into the amplicons that are generated;
d. optionally purifying the amplicons from step (c);
e. conducting a further PCR using primers specific for the universal primer binding sites incorporated in step (c);
f. optionally purifying the amplicons from step (e);
g. sequencing the amplification product from step (f); and
h. determining the presence or absence of a genomic rearrangement. If a genomic rearrangement is present, the nature of the arrangement can be determined according to the sequence of the amplicons.

Importantly, further selective enrichment steps (beyond the selective PCR step) are not necessary in the methods disclosed herein, for example using hybridisation probes, since a step of enrichment is inherently incorporated into the selective PCR. Therefore, in preferred embodiments, the methods do not comprise enrichment (for example enrichment of any sample, DNA or amplicon) by hybridisation, for example enrichment using hybridisation probes.

The DMOI and Genomic Rearrangements to be Detected

The DNA molecules of interest (DMOIs) may be single stranded or double stranded, but they are preferably double stranded. In some embodiments, the DMOI is DNA obtained by reverse transcription of RNA. Hence in some embodiments, the method comprises converting an RNA sequence to a DNA sequence to obtain the DMOI. Converting an RNA sequence to a DNA sequence may be carried out using a reverse transcriptase.

The DMOI may be cell-free DNA (cfDNA). In a preferred embodiment, the DMOI is a circulating tumour DNA (ctDNA).

The DMOI are preferably fragmented. The methods may comprise a step of fragmenting the DNA. Alternatively (and most commonly), the DNA may already be fragmented in the sample that is obtained from a patient.

In some embodiments, the DMOI are up to 500 base pairs in length.

When the DMOIs are ctDNA molecules, the ctDNA may be from a cancer selected from the group consisting of acute lymphoblastic leukemia, acute or chronic lymphocytic or granulocytic tumour, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumour, giant cell tumour, glioblastoma multiforma, hairy-cell tumour, head cancer, hyperplasia, hyperplastic corneal nerve tumour, in situ carcinoma, intestinal ganglioneuroma, islet cell tumour, Kaposi's sarcoma, kidney cancer, larynx cancer, leiomyomater tumour, liver cancer, lung cancer, lymphomas, malignant carcinoid, malignant hypercalcemia, malignant melanomas, marfanoid habitus tumour, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumour, pancreas cancer, parathyroid cancer, pheochromocytoma, polycythemia vera, primary brain tumour, prostate cancer, rectum cancer, renal cell tumour, retinoblastoma, rhabdomyosarcoma, seminoma, skin cancer, small-cell lung tumour, soft tissue sarcoma, squamous cell carcinoma, stomach cancer, thyroid cancer, topical skin lesion, veticulum cell sarcoma, and Wilm's tumour. In a preferred embodiment, the cancer is lung cancer.

The DMOI may be derived from a fusion gene or a fragment of a fusion gene. The fusion may be a fusion selected from the group consisting of CD74-ROS1, SLC34A2-ROS1, SDC4-ROS1, EZR-ROS1, GOPC-ROS1, LRIG3-ROS1, TPM3-ROS1, PPFIBP1-ROS1, EML4-ALK, BCR-ABL, TCF3-PBX1, ETV6-RUNX1, MLL-AF4, SIL-TAL1, RET-NTRK1, PAX8-PPARG, MECT1-MAML2, TFE3-TFEB, BRD4-NUT, ETV6-NTRK3, TMPRSS2-ERG, TPM3-NTRK1, SQSTM1-NTRK1, CD74-NTRK1, MPRIP-NTRK1 and TRIM24-NTRK2. In some embodiments, the fusion is a fusion between a gene selected from the group consisting of ROS1, ALK, EML4, BCR, ABL, TCF3, PBX1, ETV6, RUNX1, MLL, AF4, SIL, TAL1, RET, NTRK1, PAX8, PPARG, MECT1, MAML2, TFE3, TFEB, BRD4, NUT, ETV6, NTRK3, TMPRSS2, NKRT2 and ERG and at least one other gene. In preferred embodiments, the gene fusion is a ROS1 fusion, an ALK fusion, a NTRK1 fusion or a RET fusion. Fusion that are particular preferred are ROS1-CD74, ROS1-SLC34A2, ROS1-SDC4, ROS1-EZR, ALK-EML4, KIF5B-RET, TRIM33-RET, CCDC6-RET, NCO4A-RET, KIF5B-ALK, TPM3-NTRK1, SQSTM1-NTRK1, CD74-NTRK1, MPRIP-NTRK1.

Accordingly, the region that is targeted by the forward or reverse region-specific primers may be selected from the group consisting of ROS1, ALK, EML4, BCR, ABL, TCF3, PBX1, ETV6, RUNX1, MLL, AF4, SIL, TAL1, RET, NTRK1, PAX8, PPARG, MECT1, MAML2, TFE3, TFEB, BRD4, NUT, ETV6, NTRK3, TMPRSS2, NKRT2 and ERG. In one embodiment, the region that is targeted by the forward or reverse region-specific primers may be selected from the group consisting of ROS1, ALK, NTRK1 and RET. In one embodiment, the forward region-specific primer targets a first fusion partner and the reverse region-specific primer targets as second fusion partner, wherein the fusion partners are selected from the group consisting of CD74-ROS1, SLC34A2-ROS1, SDC4-ROS1, EZR-ROS1, GOPC-ROS1, LRIG3-ROS1, TPM3-ROS1, PPFIBP1-ROS1, EML4-ALK, BCR-ABL, TCF3-PBX1, ETV6-RUNX1, MLL-AF4, SIL-TAL1, RET-NTRK1, PAX8-PPARG, MECT1-MAML2, TFE3-TFEB, BRD4-NUT, ETV6-NTRK3, TMPRSS2-ERG, TPM3-NTRK1, SQSTM1-NTRK1, CD74-NTRK1, MPRIP-NTRK1 and TRIM24-NTRK2. In one embodiment, the fusion partners are selected from the group consisting of ROS1-CD74, ROS1-SLC34A2, ROS1-SDC4, ROS1-EZR, ALK-EML4, KIF5B-RET, TRIM33-RET, CCDC6-RET, NCO4A-RET, KIF5B-ALK, TPM3-NTRK1, SQSTM1-NTRK1, CD74-NTRK1, MPRIP-NTRK1.

In one embodiment, the method comprises the use of a pool of primers that targets at least two genes selected from the group consisting of ROS1, ALK, EML4, BCR, ABL, TCF3, PBX1, ETV6, RUNX1, MLL, AF4, SIL, TAL1, RET, NTRK1, PAX8, PPARG, MECT1, MAML2, TFE3, TFEB, BRD4, NUT, ETV6, NTRK3, TMPRSS2, NKRT2 and ERG. In one embodiment, the method comprises the use of a pool of primers that targets at least two genes selected from the group consisting of ROS1, ALK, NTRK1 and RET. Of course, more than two primer pools can be used. For example, in one embodiment, the method comprises the use of a pool of primers that targets ROS1, a pool of primers that targets ALK, a pool of primers that targets NTRK1 and a pool of primers that targets RET. Alternatively, at least 5 genes, at least 10 genes or all of the genes ROS1, ALK, EML4, BCR, ABL, TCF3, PBX1, ETV6, RUNX1, MLL, AF4, SIL, TAL1, RET, NTRK1, PAX8, PPARG, MECT1, MAML2, TFE3, TFEB, BRD4, NUT, ETV6, NTRK3, TMPRSS2, NKRT2 and ERG may be targeted in a single reaction. When a fusion between two different genes is present, a first pool targeting a first gene in the fusion acts as a pool of forward primers, and a second pool targeting the second gene in the fusion acts as a pool of reverse primers. The forward and reverse designations are arbitrary and can be swapped and are provided herein for the sake of clarity.

The fusions may be intronic fusions (a fusion between two introns), exonic fusion (a fusion between two exons) or it may be a intron/exon fusion (a fusion between an intron from one region or gene and an exon from another region or gene) or the fusion may be between two intergenic regions, or the fusion may be an intronic/intergenic or intergenic/exonic fusion. Most often the fusion will be an intronic fusion.

Fusion Calls

The present disclosure is particularly useful in determining the presence of genomic fusions. When determining the presence or absence of a gene fusion, a bioinformatic analysis may need to be undertaken to determine whether or not the detection of an amplification product from the selective PCR is actually indicative of the presence of a gene fusion. The decision on whether or not a gene fusion is present is known as a "fusion call".

Figure 8:
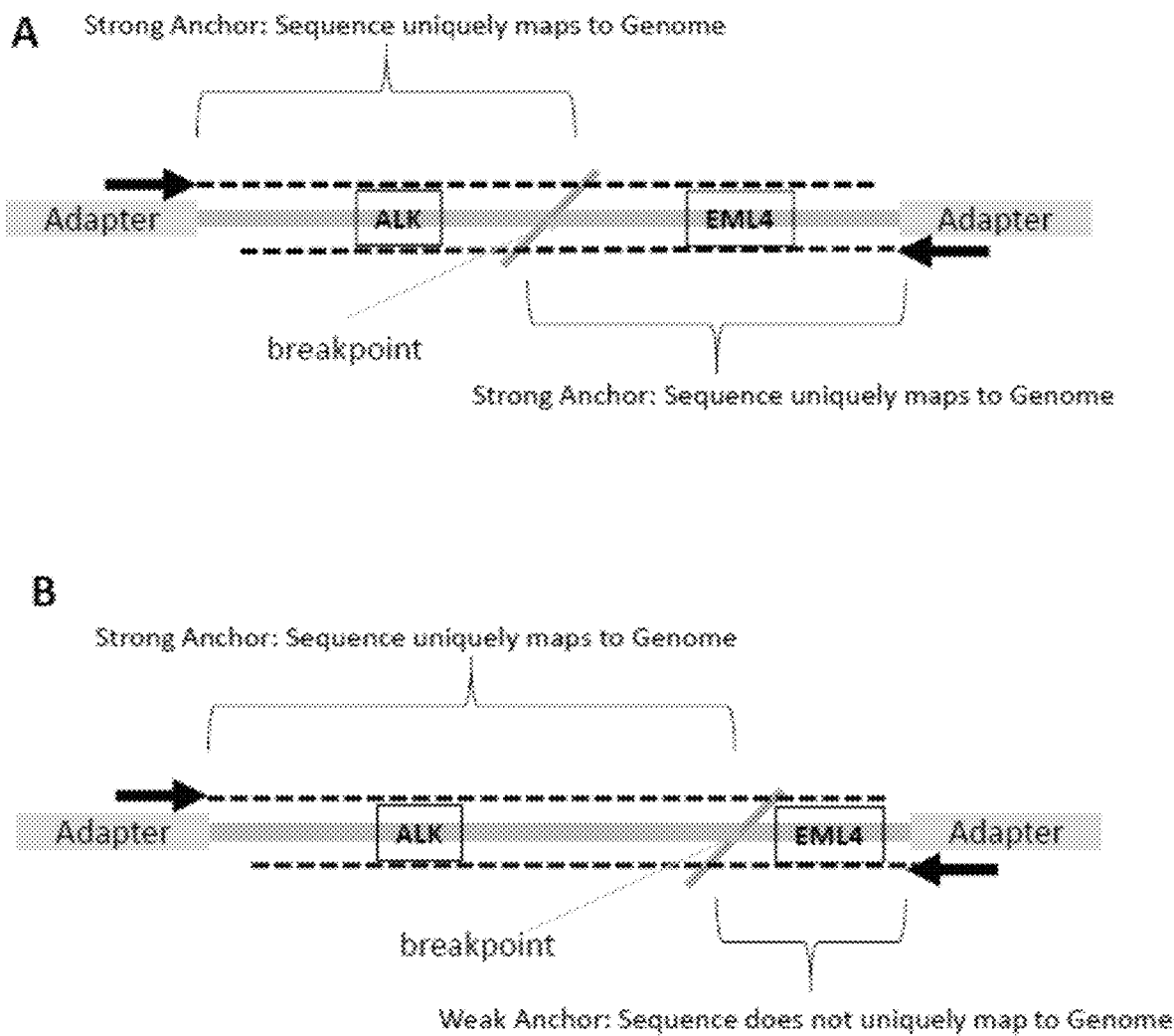
FIG. 8: Bioinformatic method for calling gene fusions: Amplicons are generated by two primer pairs amplifying a fusion event which are then sequenced (dotted line indicates read) by NGS (Black Arrows indicate sequencing primers). The analysis method involves determining the minimum number of base pairs that need to be sequenced (for each primer site) to uniquely match a target region. A strong anchor has sufficient base pairs sequenced to uniquely match a target region, a weak anchor does match a target region but also matches other regions in the reference genome, it therefore does not uniquely match the target region. The method uses the known primer binding locations to determine the expected sequence within the reads which removes the need for aligning reads to the entire reference genome. A. An amplicon has two strong anchors with both the ALK and EML4 portions of read uniquely matching an ALK or EML4 reference sequence. B. An amplicon has one strong anchor and one weak anchor. ALK portion of read uniquely matches a target region, EML4 does not uniquely match the reference genome.

As discussed for FIG. 8, amplicons are generated by two primers amplifying a fusion event which are then sequenced (dotted line indicates read) by NGS (Black Arrows indicate sequencing primers). The analysis method involves determining the minimum number of base pairs that need to be sequenced (for each primer site) to uniquely match a target region. A strong anchor has sufficient base pairs sequenced to uniquely match a target region, a weak anchor does not match only the target region but also matches other regions in the reference genome, it therefore does not uniquely match the target region. The method uses the known primer binding locations to determine the expected sequence within the reads which removes the need for aligning reads to the entire reference genome. In the example of FIG. 8a, the amplicon has two strong anchors with both the ALK and EML4 portions (in this example) of the read uniquely matching a ALK and EML4 reference sequences. In the example of FIG. 8b, the amplicon has one strong anchor and one weak anchor. The ALK portion of the read uniquely matches a target region, but the EML4 does not uniquely match the reference genome.

In some embodiments, the method comprises sequencing the reaction product from a first or subsequent PCR and matching the sequences to a reference sequence or one or more databases of reference sequences (also referred to herein as primer information databases). The reference sequences may be a reference genomic region or sequence, or one or more databases of reference genomic regions or sequences. The art may refer to "mapping", however the present methods do not entail "mapping" as it is understood in the art, since the origin of the read is inferred by the presence of sequence that matches the sequences of the primers, which have known genomic locations; and the read is compared to the expected sequences that lie downstream of the primer sequences. The term mapping on the other hand is used to describe the comparison of a sequence with a long genomic sequence, such as a human genome, and the identification of its likely origin from within this large sequence without prior knowledge. Therefore, in embodiments described herein, the analysis of the sequence read comprises matching one or more portions of the sequence read to one or primer information databases comprising a plurality of reference sequences. Since the technique is distinct from traditional mapping techniques, the reference sequences contained in the one or more primer information databases against which the one or more portions of the sequences reads are matched have a maximum length of up to 1 kb.

Methods of the disclosure may comprise comparing at least two portions of the sequence read with one or more databases of reference sequences, wherein each portion comprises the sequence of a primer binding site and an adjacent downstream (i.e. 5') sequence. The one or more databases of reference sequences may comprise the genomic location corresponding to each primer binding site in the database.

Matching the relevant portion(s) of the sequence read to a reference genomic sequence or, preferably, to one or more databases of reference genomic sequences, allows the skilled person to determine the precise genomic rearrangement event that has occurred. An advantage of the methods and kits disclosed herein is that neither prior knowledge of the presence of a genomic rearrangement, nor details of the precise rearrangement that has occurred, are needed for the method to be carried out. In addition, unnecessary sequencing of reaction products not arising from a genomic rearrangement event is not required, drastically reducing the cost and effort required to determine the presence or absence of the genomic rearrangement. Furthermore, computational power is reduced, since the methods do not comprise mapping or aligning the sequence reads or portions thereof to a reference genome, which may be very long. Instead, the sequence reads, or portions thereof, are matched to one or more databases comprising reference genomic sequences, for example wherein the reference genomic sequences have in the one or more databases have a maximum length of up to 1 kb.

Since the method is carried out on DMOIs that are derived from more than one section of a genome (when a genomic rearrangement event has occurred), methods disclosed herein may comprise matching the DMOI to two or more regions from the reference genome. For example, the method may comprise identifying two genes from which the sequence of the DMOI is derived. In the event of a genomic rearrangement, regions from each of these two genes have been brought into sufficient proximity for a specific PCR amplification product to be produced in the selective PCR carried out using the pool of forward and reverse primers.

The methods disclosed herein may comprise identifying the presence of a forward primer binding site and a reverse primer binding site and uniquely matching both to their respective genomic location. References to "uniquely matching" herein refer to being able to match a sequence to a single genomic location in a reference genome or reference genomic sequence (or database of genomic sequences). Uniquely matching can therefore only occur when there is sufficient sequence information to rule out any other locations. The length of sequence required varies according from location to location, depending on the heterogeneity of a given region. Regions that include several repeats, for example, will therefore require longer sequences to enable unique matching to take place. Other locations will only need short sequences (perhaps just the sequence of the primer itself) to uniquely match the primer to a given genomic location.

A fusion call may be made if one, but preferably both, of the forward and reverse primers and their downstream sequences can be uniquely matched to a region in the genome. For example, a fusion call may be made if the forward primer can be uniquely matched to a sequence in the first region of interest and/or if the reverse primer can be uniquely matched to a sequence in the second region of interest.

Accordingly, in one embodiment there is provided a method for determining the presence or absence of a gene fusion in a DMOI (specifically, an amplicon, since the sequence that is provided is the sequence of a product of a selective PCR), the method comprising:
 a. providing the sequence of a DMOI;
 b. determining, from a population of known primers, the location of at least one forward primer binding site and the location of at least one reverse primer binding site in the DMOI;
 c. matching the sequence of the DMOI to at least one region of interest in a reference genome;
 d. optionally determining the potential location of a gene fusion between two different regions of interest of the genome; and
 e. determining whether a gene fusion is present in the DMOI.

The DMOI is the amplification product of a PCR using the population of known forward and reverse primers (for example, the primer pools or sets disclosed herein).

In some embodiments, the method comprises matching the sequence of the DMOI to at least two different regions of interest in a reference genome. The two regions may be suspected of having undergone a genomic rearrangement or gene fusion event.

In one embodiment, there is provided a method for determining the presence or absence of a gene fusion in a DMOI, the method comprising:
 a. providing the sequence of a DMOI as a sequence read;
 b. identifying in the sequence read the presence of at least one forward primer binding site and the presence of at least one reverse primer binding site from a population of forward and reverse primers;
 c. determining the corresponding genomic locations of the forward and reverse primer binding sites by reference to the sequences of the forward and reverse primer binding sites and the sequence downstream and adjacent to the forward and reverse primer binding sites in the sequence read; and
 d. determining the presence or absence of a gene fusion in the DMOI.

The sequence read provided in step (a) is provided by sequencing one or more DMOIs from a patient sample. For example, the sequence read may provide the sequence of a ctDNA molecule obtained from a patient. The sequence of the sequence read is therefore derived from the genome of a patient, or more specifically, the genome of a tumour or other cancer present in the patient that gave rise to the ctDNA. Of course, the sequence may be provided according to any of the methods described herein for determining the presence of absence of a gene fusion event.

Step (b) comprises identifying in the sequence read the presence of at least one forward primer binding site and the presence of at least one reverse primer binding site from a population of corresponding forward and reverse primers. The forward and reverse primers correspond with the forward and reverse primer binding sites in that one is the complement of the other, such that a primer would anneal to a corresponding primer binding site. The sequences of the primers and/or the primer binding sites are known. The sequence of the primers and/or primer binding sites may be contained in one or more databases. Since the sequence reads can be provided by methods described herein, it will be apparent to the reader that the forward and reverse primers can be the pool of region-specific forward and reverse primers described above that are used to selectively amplify a gene fusion between two regions of interest.

When the presence of at least one forward and at least one reverse primer binding site in the sequence read has been identified, step (c) determines the corresponding genomic locations of the forward and reverse primer binding sites by reference to the sequences of the forward and reverse primer binding sites and the sequence downstream and adjacent to the forward and reverse primer binding sites in the sequence read. The corresponding genomic location is the original genomic location in the patient's genome or cancer that gave rise to the DMOI, which in turn gave rise to the sequence read provided in step (a). This step is determining the corresponding genomic locations for the forward and reverse primer binding sites in the genome that gave rise to the ctDNA.

The downstream sequences are adjacent, meaning immediately adjacent to the primer binding sites in the sequence read.

In step (d), when the genomic locations of the forward and reverse primer binding sites are different, or are suspected of being different, a gene fusion event is present. When the genomic locations of the forward and reverse primer binding site are the same, a gene fusion event is not present. By "different", this refers to different first and second regions of interest that were targeted by the pools of region-specific forward and reverse primers. For example, when the genomic locations of the forward and reverse primer binding sites identified in the sequence read are at least 1 kb apart in a genome that has not undergone a gene fusion, or are usually found on different chromosomes or in different genes, a gene fusion event is present in the sequence read (specifically, the DMOI that gives rise to the sequence read).

It may only be possible to uniquely match one of the forward and reverse primer binding sites in the sequence read to a corresponding location in a reference genome. However, even if it is not possible to uniquely match both forward and reverse primer binding sites in the sequence read to corresponding locations in a reference genome, a gene fusion event can still be predicted. For example, if a first primer binding site in a sequence read is uniquely matched to a genomic location, the second primer binding site may be matched to a plurality of different genomic locations. If all of those locations are different to the location that has been uniquely identified as giving rise to the first primer binding site in the sequence read, then a gene fusion is still likely to be present. Therefore, the step of determining the corresponding genomic locations of the forward and reverse primer binding sites by reference to the sequences downstream and adjacent to the forward and reverse primer binding sites in the sequence read may comprise matching at least one of the forward and reverse primer binding sites in the sequence read to a unique genomic location. The other primer binding site in the sequence read may be matched to one or more genomic locations.

In one embodiment, the method comprises:
a. providing the sequence of a DMOI as a sequence read;
b. identifying in the sequence read the presence of at least one forward primer binding site and the presence of at least one reverse primer binding site from a population of corresponding forward and reverse primers whose sequences are known;
c. when the presence of at least one forward and at least one reverse primer binding site in the sequence read has been identified, determining the corresponding genomic locations of the forward and reverse primer binding sites by reference to the sequences of the forward and reverse primer binding sites and the sequences downstream of and adjacent to the forward and reverse primer binding sites in the sequence read; and
d. determining the presence or absence of a gene fusion in the DMOI, wherein when the forward and reverse primer binding sites are in different genes, a gene fusion event is present.

The step of determining the corresponding genomic locations of the forward and reverse primer binding sites refers to uniquely identifying the genomic sequence in a reference genome that gave rise to the sequence of at least one of the forward or reverse primer binding sites. In one embodiment, the step of determining the corresponding genomic locations of the forward and reverse primer binding sites refers to uniquely identifying the genomic sequence in a reference genome that gave rise to the sequence of both the forward and reverse primer binding sites.

In some embodiments, the step of identifying the presence of the at least one forward and at least one reverse primer binding site in the sequence read and the step of determining the corresponding genomic locations of the forward and reverse primer binding sites comprises interrogating one or more databases. The one or more databases may comprise:

a. the genomic location for each forward and reverse primer binding site in the primer population;
b. the sequence of each forward and reverse primer binding site in the primer population;
c. the downstream sequence in the corresponding genomic location for each of the forward and reverse primer binding sites in the primer population (optionally wherein the length of the downstream sequence is at least 1 base pair); and
d. the minimum number of base pairs downstream of each primer binding site required to uniquely match a primer binding site from a sequence read to the corresponding genomic location.

Accordingly, for each forward and reverse primer in the primer population, the database or databases comprise:
a. the genomic location for the primer binding site;
b. the sequence of the primer binding site (and/or the sequence of the corresponding primer);
c. the sequence downstream of and adjacent to the primer binding site in the corresponding genome (or at the corresponding genomic location, optionally wherein the length of the downstream sequence is at least 1 base pair) and
d. the minimum number of base pairs downstream of the primer binding site required to uniquely match a primer binding site from a sequence read to the corresponding location in the genome.

The database may further comprise the location and/or identify of SNPs or other polymorphisms. For example, the downstream sequence for each of the primers may take into account the presence of polymorphisms (including SNPs, LTRs, STRs) to assist accurate identification. The inclusion of polymorphisms assists the use of the database across broader patient populations.

In some embodiments, the step of interrogating the one or more databases comprises comparing the sequence downstream of the forward and reverse primer binding sites in the sequence read with the corresponding downstream sequences in the one or more databases. In other words, the method compares the sequences downstream of the forward and reverse primer binding sites in the sequence read with the downstream sequences provided in the database(s) for the corresponding forward and reverse primers.

The database or databases may be referred to as primer databases or primer information databases. The information may be spread across multiple databases. For example, one database may contain the sequence of each primer in the primer population and assign each primer in the primer population a unique label. The label can then be used to interrogate a separate database that provides the remaining information (such as the downstream sequences and length of downstream sequence required to uniquely map the primer to a specific region in a corresponding genome) arranged according to the unique labels of the primers. The specific arrangement and storage of the information is therefore not crucial.

The method may comprise determining the "anchor strength" of the forward and reverse primer binding sites in the sequence read, wherein:
a. a weak anchor is defined as a primer binding site in a sequence read having a downstream sequence in the sequence read that matches the downstream sequence in the corresponding primer in the primer database, but said matching downstream sequence in the sequence read is shorter than the length of the downstream sequence required in the database of reference genomic sequences to uniquely match the sequence obtained to the corresponding genomic location; and b. a strong anchor is defined as a primer binding site in a sequence read having a downstream sequence in the sequence read that matches the downstream sequence in the corresponding primer in the primer database, and said matching downstream sequence in the sequence read is equal to or longer than the length of the downstream sequence required in the database of reference genomic sequences to uniquely match the sequence obtained to the corresponding genomic location.

In some embodiments, a gene fusion is called when both the forward and reverse primer binding sites are identified as strong anchors. In other embodiments, a gene fusion is called when at least one of the forward and reverse primer binding sites is identified as a strong anchor.

In one embodiment, the method comprises
a. providing the sequence of a DMOI as a sequence read;
b. interrogating one or more primer information databases to:
  i. identify in the sequence read the presence of at least one forward primer binding site and the presence of at least one reverse primer binding site from a population of forward and reverse primers; and
  ii. determine the corresponding genomic locations of the forward and reverse primer binding sites;
c. wherein the one or more primer information databases comprise:
  i. the genomic location for each forward and reverse primer binding site in the primer population;
  ii. the sequence of each forward and reverse primer binding site in the primer population;
  iii. the downstream sequence in the corresponding genomic location for each of the forward and reverse primer binding sites in the primer population; and
  iv. the minimum number of base pairs downstream of each primer binding site required to uniquely match a primer binding site from a sequence read to a given genomic location; and
c. determining the presence or absence of a gene fusion in the DMOI.

The step of interrogating the database to identify in the sequence read the presence of at least one forward primer binding site and the presence of at least one reverse primer binding site may comprise comparing the sequence of the sequence read (or portions thereof) with the forward and reverse primer binding site sequences in the primer information database. The sequence of each forward and reverse primer binding site in the primer population and their corresponding downstream sequences may be referred to as the reference sequences (or reference genomic sequences). It is against these reference sequences the sequence read (or portions thereof) are matched. Specifically, the primer binding sites in the sequence read may be compared to the sequences in the one or more databases corresponding to the forward and reverse primer binding sites in the primer population (part (ii) of the database above) and the adjacent downstream sequence in the sequence read may be compared to the corresponding downstream sequences in the matching genomic location (part (iii) of the database above). In some embodiments, the maximum length of the sequences in (ii) and (iii) above is 1 kb.

The step of determining the corresponding genomic locations of the forward and reverse primer binding sites may comprise comparing the sequences downstream of the forward and reverse primer binding sites in the sequence read with the downstream sequences provided in the one or more primer information databases. A unique genomic location may be assigned to the forward and/or reverse primer binding site from the sequence read when the downstream sequence in the sequence read is the same as the or a downstream sequence for a corresponding primer in the primer information database and the length of the downstream sequence in the sequence read that is the same as the or a downstream sequence for the corresponding primer in the primer information database is equal to or greater than the minimum number of base pairs downstream of the primer binding site required to uniquely match the primer binding site from a sequence read to the corresponding genomic location.

Of course, interrogation of the database may provide a plurality of genomic locations for each of the primer binding sites in the sequence reads, depending on the strength of the anchor. Accordingly, in one embodiment, the method comprises identifying all the possible genomic locations for both the forward and reverse primer binding sites in the sequence read.

A fusion may be called when at least one of the forward or reverse primers is uniquely matched to a genomic location that is different to all of the possible genomic locations identified for the other primer binding site in the sequence read.

In one embodiment, the method comprises
a. providing the sequence of a DMOI as a sequence read;
b. providing one or more primer information databases, wherein the one or more primer information databases comprise:
  i. the genomic location for each forward and reverse primer binding site in a primer population;
  ii. the sequence of each forward and reverse primer binding site in the primer population;
  iii. the downstream sequence in the corresponding genomic location for each of the forward and reverse primer binding sites in the primer population; and
  iv. the minimum number of base pairs downstream of each primer binding site required to uniquely match a primer binding site from a sequence read to a given genomic location; and
c. comparing the sequence of the sequence read with the forward and reverse primer binding site sequences in the one or more primer information databases to identify in the sequence read the presence and identity of at least one forward primer binding site and the presence and identity of at least one reverse primer binding site from the population of forward and reverse primers;
d. comparing the sequences downstream of the forward and reverse primer binding sites in the sequence read with the corresponding downstream sequences provided in the one or more primer information databases;
e. assigning to the forward and/or reverse primer binding site from the sequence read the corresponding genomic location of the primer binding site in the one or more primer information databases when:
  i. the downstream sequence in the sequence read is the same as the downstream sequence for the corresponding primer in the primer information database; and
  ii. the length of the downstream sequence in the sequence read that is the same as the downstream sequence for the corresponding primer in the primer information database is equal to or greater than the minimum number of base pairs downstream of the primer binding site required to uniquely match the primer binding site from the sequence read to the corresponding genomic location;

f. determining the presence or absence of a gene fusion in the DMOI, wherein a gene fusion is present when the forward and reverse primer binding sites in the sequence read are assigned different genomic locations.

In one embodiment, the method comprises a. providing the sequence of a DMOI as a sequence read;
b. providing one or more primer information databases, wherein the one or more primer information databases comprise:
  i. the genomic location for each forward and reverse primer binding site in a primer population;
  ii. the sequence of each forward and reverse primer binding site in the primer population;
  iii. the downstream sequence in the corresponding genomic location for each of the forward and reverse primer binding sites in the primer population; and
  iv. the minimum number of base pairs downstream of each primer binding site required to uniquely match a primer binding site from a sequence read to a given genomic location; and
c. comparing the sequence of the sequence read with the forward and reverse primer binding site sequences in the one or more primer information databases to identify in the sequence read the presence and identity of at least one forward primer binding site and the presence and identity of at least one reverse primer binding site from the population of forward and reverse primers;
d. comparing the sequences downstream of the forward and reverse primer binding sites in the sequence read with the corresponding downstream sequences provided in the one or more primer information databases;
e. assigning to the forward and/or reverse primer binding site from the sequence read the corresponding genomic location of the primer binding site in the one or more primer information databases when:
  i. the downstream sequence in the sequence read is the same as the downstream sequence for the corresponding primer in the primer information database; and
  ii. the length of the downstream sequence in the sequence read that is the same as the downstream sequence for the corresponding primer in the primer information database is equal to or greater than the minimum number of base pairs downstream of the primer binding site required to uniquely match the primer binding site from the sequence read to the corresponding genomic location;
f. determining the presence or absence of a gene fusion in the DMOI, wherein a gene fusion is present when at least one of the forward and reverse primer binding sites in the sequence read is assigned to only one genomic location (i.e. is a strong anchor). The other primer binding site in the sequence read may be assignable to a plurality of genomic locations, for example if the downstream sequence in the sequence read does not match the expected downstream sequence in the one or more primer information databases, or the downstream sequence in the sequence read does match the excepted downstream in the one or more primer information databases, but the matching downstream sequence is not of sufficient length (i.e. it is a weak anchor). However, one can still be confident of a fusion if all the genomic locations for this weak anchor that are assignable to it are all different from the genomic location assigned to the strong anchor.

"Genomic locations" can also refer simply to genes. Hence, a gene fusion may be present when at least one of the forward and reverse primer binding sites in the sequence read is assigned to only one gene and the other primer binding site in the sequence read is assigned to a plurality of genes that are all different from the gene assigned to the first primer binding site in the sequence read.

The methods disclosed herein can be carried out without having to align or map the sequence reads or portions thereof to a reference genomic sequence. In some embodiments, the methods disclosed herein can be carried out without having to align or map the sequence reads or portions thereof to a reference genomic sequence that is more than 10 kb in length, since only the sequences in the one or more primer information databases need to be interrogated.

The forward and reverse primer population includes the primers used in the assays to detect the genomic rearrangement and to provide the sequence reads. The one or more primer information database therefore includes the corresponding information relating to the primer pools of the present invention. The database also takes into account polymorphisms in the different genomic locations covered by the primer population. For example, a given primer in the primer pool might have a plurality of downstream sequences that differ according to the polymorphisms located at that region of the genome. Accordingly, the database or databases may comprise the sequence or at least one downstream sequence that is adjacent to the primer binding site in the corresponding genome for each primer in the one or more primer information databases.

The databases described herein contain sufficient information to enable to skilled person to compare the potential primer binding site identified in the sequence read with the primer binding sites of the primers present in the pool of primers used to generate the sequence read. If the sequence of the primer binding site itself uniquely matches the genome (for example because the primer binding site is of sufficient length and/or it is present in a particularly heterogeneous section of the reference genome) then the sequence of the primer itself may be sufficient to uniquely match the corresponding region in the DMOI to a unique position in the reference genome. However, if the primer binding site is not sufficiently long (or is in a less heterogeneous section of the reference genome), then additional downstream sequences (i.e. on the 3' side of the primer binding site) are required to determine a unique position in the genome. Hence for some (and indeed most) primers it is necessary to include the downstream sequences. The skilled person can make a comparison between the sequence that is downstream of the primer binding site in the sequence to see if it matches the expected downstream sequence for a given genomic location.

In some embodiments, the primer information database or database comprise the downstream sequences of at least 50% of the primers in the primer pool. Preferably the reference database includes the downstream sequence for all primers that do not themselves uniquely match the reference genome. The length of the downstream sequence can vary according to the primer and its binding site. In some embodiments, the length of the downstream sequences is at least 1 nucleotide. Preferably the length is at least 10 nucleotides. The downstream sequences are generally immediately adjacent to the primer binding sites (there are no nucleotides between the last nucleotide of the primer binding site and the first nucleotide of the downstream sequence).

In some embodiments a fusion call may be made when both primer binding sites are strong anchors. However, a fusion call still can be made with only one strong anchor. Nevertheless, when the primer binding site is close to the location of the gene fusion in the sequence read, there may only be a small number of nucleotides that are the same between the sequence read and the reference downstream genomic sequence. To make a fusion call for only one strong anchor, it is preferred the match between the downstream sequence in the DMOI and the downstream sequence in the reference primer database is at least 5 nucleotides, optionally at least 10 nucleotides. Therefore, in one embodiment, the method comprises determining the distance of each of the primer binding sites from the potential location of the gene fusion in the sequence read.

The downstream sequences provided in the one or more primer information databases will be derived from a reference genome. The reference genome will be one that is suitable for the analysis that is being undertaken. For example, for an analysis carried out on sequences derived from a human sample, a human genome will be used as a reference genome and the source for the downstream sequences (a complete or partial human genome). "Reference genome" herein includes fragments of a genome that correspond to the regions of interest, for example specific genes that have undergone a genomic rearrangement event (or are suspected of having undergone such a rearrangement). The genomic locations that are determined are the genomic locations in the reference genome or partial reference genome.

The step of matching or comparing a sequence downstream of the forward and reverse primer binding sites in the sequence read to at least one downstream genomic location in a one or more databases may comprise: for a given primer binding site, interrogating the one or more primer databases for a corresponding downstream sequence, and comparing the downstream sequence from the primer database to the sequence downstream of the primer binding site in the sequence read.

The method may comprise a step of determining the potential location of a gene fusion between two different primer binding sites in the sequence read. In one embodiment, the method therefore comprises matching a portion of the sequence read (including the sequence of a forward primer binding site) to a first genomic location and matching a different portion of the sequence read (including the sequence of a reverse primer binding site) to a second genomic location.

Of course, the fusion call methods disclosed herein can be combined with the methods of determining the presence of a genomic rearrangement event (such as a gene fusion) disclosed herein. For example, in one embodiment the method comprises:
 a. contacting a sample comprising DNA molecules of interest (DMOIs) with a pool of at least 20 region-specific forward primers and a pool of at least 20 region-specific reverse primers, wherein:
  i. each of the forward primers in the forward primer pool comprises a sequence specific for a first region of interest and a first primer binding site; and
  ii. each of the reverse primers in the reverse primer pool comprises a sequence specific for a second, different, region of interest and a second primer binding site;
 b. amplifying the DMOIs using the region-specific primers;
 c. conducting PCR using forward primers that target the first primer binding site and reverse primers that target the second primer binding site;
 d. sequencing the PCR amplification product to provide a library of sequence reads, wherein the sequence reads comprise the sequence of a forward and/or reverse primer used in step (a);
 e. identifying in at least one of the sequence reads the presence of at least one region-specific forward primer binding site and the presence of at least one region-specific reverse primer binding site from the pool of forward and reverse primers;
 f. determine the corresponding genomic locations of the forward and reverse primer binding sites by reference to the sequences of the forward and reverse primer binding sites and the sequences downstream and adjacent to the forward and reverse primer binding sites in the sequence read;
 g. determining the presence or absence of a gene fusion in the DMOI.

Of course, the more detailed analysis methods can also be combined with the different embodiments relating to the processing and sequencing of the DMOIs.

For example, one embodiment provides:
 a. contacting a sample comprising DNA molecules of interest (DMOIs) with a pool of at least 20 region-specific forward primers and a pool of at least 20 region-specific reverse primers, wherein:
  i. each of the forward primers in the forward primer pool comprises a sequence specific for a first region of interest and a first primer binding site; and
  ii. each of the reverse primers in the reverse primer pool comprises a sequence specific for a second, different, region of interest and a second primer binding site;
 b. amplifying the DMOIs using the region-specific primers;
 c. conducting PCR using forward primers that target the first primer binding site and reverse primers that target the second primer binding site;
 d. sequencing the PCR amplification product to provide a library of sequence reads, wherein the sequence reads comprise the sequence of a forward and/or reverse primer used in step (a);
 e. providing one or more primer information databases, wherein the one or more primer information databases comprise:
  i. the genomic location for each forward and reverse primer binding site in a primer population;
  ii. the sequence of each forward and reverse primer binding site in the primer population;
  iii. the downstream sequence in the corresponding genomic location for each of the forward and reverse primer binding sites in the primer population; and
  iv. the minimum number of base pairs downstream of each primer binding site required to uniquely match a primer binding site from a sequence read to a given genomic location; and
 f. comparing the sequence of the sequence reads with the forward and reverse primer binding site sequences in the one or more primer information databases to identify in at least one of the sequence reads the presence and identity of at least one forward primer binding site and the presence and identity of at least one reverse primer binding site from the population of forward and reverse primers;
 g. comparing the sequences downstream of the forward and reverse primer binding sites in the sequence read with the corresponding downstream sequences provided in the one or more primer information databases;

h. assigning to the forward and/or reverse primer binding site from the sequence read the corresponding genomic location of the primer binding site in the one or more primer information databases when:
   i. the downstream sequence in the sequence read is the same as the downstream sequence for the corresponding primer in the primer information database; and
   ii. the length of the downstream sequence in the sequence read that is the same as the downstream sequence for the corresponding primer in the primer information database is equal to or greater than the minimum number of base pairs downstream of the primer binding site required to uniquely match the primer binding site from the sequence read to the corresponding genomic location;

i. determining the presence or absence of a gene fusion in the DMOI, wherein a gene fusion is present when the forward and reverse primer binding sites in the sequence read are assigned different genomic locations.

Additional steps may also be taken to help identify fusion calls. For example, an assessment may be made to determine if the detected or suspected fusion is an in-frame fusion. If the detected or suspected fusion is not an in-frame fusion, it may be discarded and not called as a true fusion. More specifically, it has been noted by the present inventors that the vast majority of true gene fusion events, in particular in cancer patients, result in in-frame products when the DNA is transcribed to RNA. Although most gene fusion events occur between introns, the newly adjacent exons (i.e. those brought into closer proximity as a result of the gene fusion) are paired such that the coding frame matches. For example, one end of an exon may end at the $3^{rd}$ base of the codon reading frame, and the adjacent end of the next exon still start at the $1^{st}$ base of the codon reading frame. Alternatively, one end of an exon may end at the $2^{nd}$ base of the codon reading frame, and the adjacent end of the next exon still start at the $3^{rd}$ base of the codon reading frame, or one end of an exon may end at the $1^{st}$ base of the codon reading frame, and the adjacent end of the next exon still start at the $2^{nd}$ base of the codon reading frame. By reviewing the sequencing information provided by the methods disclosed herein, and once the location of the genomic breakpoint has been uniquely matched to a genome, the skilled person can correlate the gene fusion with the newly adjacent exons and determine if the resulting RNA transcript would produce an in-frame product. If it would not, the call can be discarded as not being a true gene fusion event. It is noted that the precise location of a breakpoint in an intron is not relevant to determining whether or not the breakpoint would produce an in-frame product. This is because, when the introns are removed, the adjacent exons are brought together, and the DNA is subsequently transcribed into RNA. Therefore, it is simply the pairings of newly adjacent exons that needs to be analysed when determining if an in-frame product will be produced. Accordingly, one embodiment comprises identifying the exons that are now adjacent as a result of the gene fusion and determining if the fusion would result in an in-frame product according to the last nucleotide base of one exon and the first nucleotide base of the next exon.

For example, in one embodiment, the location of the genomic breakpoint is used to predict whether a resulting RNA fusion product would be spliced to produce an in-frame product. Only fusion breakpoints predicted to produce an in-frame product are called as a gene fusion event.

Conducting such an additional analysis step helps to further check for artefacts, such as non-specific amplification and false positives and identify true variants.

In one embodiment, the method comprises determining whether the detected gene fusion would result in an in-frame product when the DNA is translated to RNA. A fusion call is made when the detected gene fusion would result in an in-frame product when the fused DNA is translated to RNA.

The present disclosure also provides the primer information databases described herein. In one aspect, the invention provides one or more primer information databases, the one or more primer databases comprising or collectively comprising, for a population of primers:
   i. the genomic location for each forward and reverse primer binding site in the primer population;
   ii. the sequence of each forward and reverse primer binding site in the primer population;
   iii. the downstream sequence in the corresponding genomic location for each of the forward and reverse primer binding sites in the primer population; and
   iv. the minimum number of base pairs downstream of each primer binding site required to uniquely match a primer binding site from a sequence read to a given genomic location.

The one or more databases disclosed herein may be provided on a computer readable storage medium. The present disclosure therefore provides a computer readable storage comprising the one or more primer information databases disclosed herein.

Interrogation of the one or more databases may be carried out using a computer. Similarly, the methods of analysing the sequence reads may be conducting using a computer.

Samples

The DMOIs may be contained in or derived from a sample from a patient. In some embodiments, the sample is a biological sample obtained from a subject, or a sample containing DMOIs that is extracted from a biological sample obtained from a subject. The patient sample can be a tissue sample, for example a surgical sample. Preferably the sample is a liquid biopsy sample, such as blood, plasma, serum, urine, seminal fluid, stool, sputum, pleural fluid, ascetic fluid, synovial fluid, cerebrospinal fluid, lymph, nipple fluid, cyst fluid, or bronchial lavage. In some embodiments the sample is a cytological sample or smear or a fluid containing cellular material, such as cervical smear, nasal brushing, esophageal sampling by a sponge (cytosponge), endoscopic/gastroscopic/colonoscopic biopsy or brushing, cervical mucus or brushing.

Many of the above samples can be obtained non-invasively, and can therefore be taken regularly without great risk or discomfort to the subject. Methods disclosed herein may comprise a step of obtaining a sample from a patient. Alternatively, the methods may be carried out on samples previously obtained from a patient (i.e., ex vivo/in vitro methods). In one embodiment, samples and/or DMOIs of interest are obtained by an in vivo/ex vivo nucleic acid harvesting technique—for example dialysis or functionalised wire.

Samples may be obtained from patients suspected of having a particular disease or condition, such as cancer. Such a disease or condition can be diagnosed, prognosed, monitored and therapy can be determined based on the methods, systems and kits described herein. Samples may be obtained from humans or from animals, such as a domesticated animal, for example a cow, chicken, pig, horse, rabbit, dog, cat, or goat. Usually, a sample will be derived from a human.

To obtain a blood sample, any technique known in the art may be used, e.g., a syringe or other vacuum suction device. A blood sample can be optionally pre-treated or processed prior to tagging and analysis. Examples of pre-treatment steps include the addition of a reagent such as a stabiliser, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a crosslinking reagent. In addition, plasma may be obtained from the blood sample, and the plasma be used in the subsequent analysis.

When obtaining a sample from a human or an animal (e.g., blood sample), the amount can vary depending upon human or animal size and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

A sample may be processed prior to undergoing further analysis. Such processing steps may comprise purification (for example removal of cells and/or debris from the sample), extraction or isolation of the DMOI. In the case of, for example, blood samples, the DMOI may be extracted from the blood sample for analysis. The amount of DNA present in the extracted sample may also be quantified prior to analysis.

In some embodiments, the sample may be obtained from the patient by an in vivo/ex vivo nucleic acid harvesting technique—for example dialysis or functionalised wire.

In particular embodiments, the method comprises a step of obtaining the sample from a patient. In other embodiments, the sample or DMOI is simply provided, as a sample was obtained at a prior point in time. The skilled person is aware of suitable techniques for obtaining, storing, stabilising and/or transporting samples prior to analysis.

In some embodiments, the DMOI is contained in or derived from a patient sample, and the patient sample is processed prior to analysis to determine the presence or absence of a genomic rearrangement. In some embodiments, the method comprises:
 a. purification of the sample to obtain a purified sample comprising the DMOIs (for example removal of cells and/or debris from the sample); and/or
 b. extraction or isolation of the DMOIs from the patient sample.

In one embodiment, the method comprises obtaining a blood sample from a patient, obtaining plasma from the blood sample, and optionally extracting the DMOIs from the plasma sample.

Methods disclosed herein may also comprise a step of purifying the amplicons from the amplification product after the or each PCR step.

Additional steps may be taken to minimise false positives and increase sensitivity of the methods. For example, in preferred embodiments, methods disclosed herein can be carried out more than once (e.g. at least twice) to minimise false positives or negatives. In preferred embodiments, the methods disclosed herein are carried out on two or more samples derived from a patient, or a patient sample is split into two or more test samples (prior to or after processing of the patient sample) and the methods are carried out on the two or more test samples. Carrying out the methods in duplicate can help to eliminate false positives, avoiding unnecessary sequencing of nucleic acids, and also increases the sensitivity of the assay. When the methods are repeated in this way, the method may comprise comparing the analysis from the two samples or two test samples. In some embodiments comprising this comparison step, the presence of a PCR amplification product from the selective PCR in both samples or both test samples is indicative of a genomic rearrangement event. As such, a fusion call is only made when a genomic rearrangement is detected in both samples or both test samples. The presence of strong or weak anchors may influence the decision on a fusion call, as discussed above.

Other Methods of the Invention

The present disclosure provides a method, the method comprising:
 a. providing a sample from a patient, said sample comprising one or more DMOI (in particular cell-free DNA, such as ctDNA); and
 b. determining the presence or absence of a genomic rearrangement event according to a method disclosed herein.

The method may further comprise processing of the sample (for example extracting or isolating the DMOI from the patient sample) prior to determining the presence or absence of a genomic rearrangement.

Other such methods disclosed herein include a method of diagnosing disease (such as cancer), a method of determining disease prognosis (such as cancer prognosis), a method of determining disease remission or relapse (such as cancer remission or relapse), a method of detecting progression of disease (such as cancer), or a method of determining the presence or absence of residual disease (such as residual cancer, wherein the DMOI is circulating tumour DNA (ctDNA)).

Regarding such methods, the methods may comprise determining the presence or absence of a genomic rearrangement in a patient using a method disclosed herein. For example, the method may comprise providing a sample from a patient, said sample comprising a plurality of cell-free DNA (cfDNA) molecules (DMOIs), optionally processing the sample, and determining the presence or absence of the genomic rearrangement. The nature and/or abundance of the genomic rearrangement being detected may be indicative of the presence of disease, the prognosis of the disease, disease remission, disease relapse, disease progression, or the presence of residual disease.

In preferred embodiments, the genomic rearrangement event is a gene fusion event, such as a ROS1 fusion, ALK fusion, RET fusion or NTRK1 fusion. The cancer may be any cancer, but of particular interest is lung cancer.

In some embodiments, the methods comprise determining the presence and/or abundance of a genomic rearrangement in a sample from a patient who has previously had a sample analysed according to a method disclosed herein.

The present disclosure also provides methods of treating disease, such as cancer. The method may comprise the steps of:
 a. providing a sample from a patient, said sample comprising one or more cell-free DNA molecules of interest (DMOIs);
 b. determining the presence or absence of a genomic rearrangement event according to a method disclosed herein; and
 c. administering a treatment, such as a therapy, to the patient, or recommending a treatment to the patient.

The step of administering or recommending a treatment/therapy will be dependent on the analysis in step b). For example, it may be the case that no disease is detected and hence no treatment is required. Alternatively, the method may detect cancer relapse, and hence treatment would be necessary. In some embodiments, the method may recommend the patient for treatment based on the presence or absence of the genomic rearrangement event. In some embodiments, the method comprises characterising the patient's disease (such as cancer) and administering or recommending the patient for an appropriate treatment.

When the disease is cancer, example treatments may include chemotherapy, radiotherapy, immunotherapy, targeted therapy and/or surgery.

Typical chemotherapeutic agents include alkylating agents (for example nitrogen mustards (such as mechlorethamine, cyclophosphamide, melphalan, chlorambucil, ifosfamide and busulfan), nitrosoureas (such as N-Nitroso-N-methylurea (MNU), carmustine (BCNU), lomustine (CCNU) and semustine (MeCCNU), fotemustine and streptozotocin), tetrazines (such as dacarbazine, mitozolomide and temozolomide), aziridines (such as thiotepa, mytomycin and diaziquone), cisplatins and derivatives thereof (such as carboplatin and oxaliplatin), and non-classical alkylating agents (such as procarbazine and hexamethylmelamine)), antimetabolites (for example anti-folates (such as methotrexate and pemetrexed), fluoropyrimidines (such as fluorouracil and capecitabine), deoxynucleoside analogues (such as cytarabine, gemcitabine, decitabine, Vidaza, fludarabine, nelarabine, cladribine, clofarabine and pentostatin) and thiopurines (such as thioguanine and mercaptopurine)), anti-microtubule agents (for example *Vinca* alkaloids (such as vincristine, vinblastine, vinorelbine, vindesine, and vinflunine) and taxanes (such as paclitaxel and docetaxel)), platins (such as cisplatin and carboplatin), topoisomerase inhibitors (for example irinotecan, topotecan, camptothecin, etoposide, doxorubicin, mitoxantrone, teniposide, novobiocin, merbarone, and aclarubicin), and cytotoxic antibiotics (for example anthracyclines (such as doxorubicin, daunorubicin apirubicin, idarubicin, pirarubicin, aclarubicin, mitoxantrone), bleomycins, mitomycin C, mitoxantrone, and actinomycin), and combinations thereof.

For lung cancer patients, in particular non-small-cell lung carcinoma (NSLC) patients, the treatment may include EGFR Inhibitors (such as erlotinib (Tarceva), afatinib (Gilotrif), gefitinib (Iressa) or osimertinib (Tagrisso)), Alk inhibitors (such as crizotinib (Xalkori), ceritinib (Zykadia) or alectinib (Alecensa), Met Inhibitors (such as tivantinib (ARQ197), cabozantinib (XL184) or crizotinib), or ROS1 inhibitors (such as Foretinib or crizotinib).

The treatment may comprise surgery, for example resection of a tumour. In particular, resection may be recommended if metastasis or disease progression has been predicted or is suspected.

The present disclosure also provides a method of determining a treatment regimen for a patient or a patient suspected of having disease (such as cancer), comprising:
 a. providing a sample from a patient, said sample comprising one or more cell-free DNA molecules of interest (DMOIs);
 b. determining the presence or absence of a genomic rearrangement event according to a method disclosed herein; and
 c. selecting a treatment regimen for the patient according to the presence or absence of a genomic rearrangement in the one or more DMOIs.

In one embodiment there is provided a method of predicting a patient's responsiveness to a treatment, such as a cancer treatment, comprising:
 a. providing a sample from a patient, said sample comprising one or more cell-free DNA molecules of interest (DMOIs);
 b. determining the presence or absence of a genomic rearrangement event according to a method disclosed herein;
 c. predicting a patient's responsiveness to a cancer treatment according to the presence or absence of a genomic rearrangement in the one or more DMOIs.

Methods of determining the present or absence of a genomic rearrangement event include methods of characterising a genomic rearrangement event or methods of characterising a patients' disease.

The methods of the present disclosure also allow detection of minimal residual disease in patients. For example, following treatment for cancer, the methods disclosed herein may be used to detect residual disease using a sample obtained from the patient. The potential for relapse can therefore be detected early and appropriate additional treatment steps be taken.

Methods of generating reports are also provided herein. For example, in one embodiment there is provided a method of generating a report, comprising:
 a. providing a sample from a patient, said sample comprising one or more cell-free DNA molecules of interest (DMOIs);
 b. determining the presence or absence of a genomic rearrangement event according to a method as described herein;
 c. generating a report comprising a listing of genomic rearrangement events determined to be present in step (b).

The report may additionally or alternatively provide the genomic coordinates of a genomic rearrangement determining in step (b). The report may further provide or suggest suitable treatments for the patient according to the genomic rearrangements determined in step (b).

A report may be generated in any of the diagnostic or prognostic methods described herein. For example, the report may include a prediction of a patient's responsiveness to a treatment, a suitable treatment regimen for a patient, a diagnosis (for example a cancer diagnosis), a disease prognosis (such as a cancer prognosis), a determining of disease remission or relapse (for example cancer remission or relapse), a responsiveness of a patient to a therapy (for example to cancer therapy), a detection of disease progression (such as cancer progression), a determination of the present or absence of residual disease (such as residual cancer), etc.

Kits and Primer Pools

The present disclosure also provides kits comprising different components used in the methods disclosed herein. A kit of parts disclosed herein may comprise a plurality of forward primers and a plurality of reverse primers suitable for detecting a genomic rearrangement event (such as a gene fusion). The forward primers are each specific for a first region of interest, and the reverse primers are each specific for a second, different, region of interest. In one embodiment, the first and second regions of interest are in different genes. The different regions of interest or different genes are located on different chromosomes when a genomic rearrangement event has not occurred. A plurality of primers is referred to herein as a set or pool of primers. References to "multiple" primers herein refer to a collection of at least two primers, but preferably at least 20 forward and at least 20 reverse primers are used. Primers targeted to regions suspected of being involved in a genomic rearrangement event are referred to as the selective PCR primers or region-specific primers.

In some embodiments, the first and second regions of interest are located on the same chromosome but are located such that little PCR amplification product (or only non-specific PCR amplification product) is generated in the absence of a genomic rearrangement event when the forward and reverse primers are used in a PCR. In some embodiments, the first and second regions of interest are located on the same chromosome but are separated by at least 160 base pairs. When more than two regions of interest are targeted, each region is separated from all the other targeted regions in the primer kit.

In certain embodiments, the forward primers tile the first region of interest and/or the reverse primers tile the second region of interest. The forward and/or reverse primers may tile the first and/or second region of interest at intervals of from about 10 to about 2000 base pairs, from about 10 to about 1000 base pairs, from about 10 to about 500 base pairs, from about 10 to about 250 base pairs, from about 10 to about 150 base pairs, from about 25 to about 125 base pairs, from about 50 to about 100 base pairs, or from about 60 to about 90 base pairs. In one embodiment, the forward and reverse primers tile the first and second region of interest, respectively, at intervals from about 60 to about 90 base pairs.

In some embodiments, the forward and reverse primers tile the first and second region of interest, respectively, at intervals of up to about 50, about 100, about 150, about 250, about 500, about 1000, about 2000 or about 2500 base pairs. In one embodiment, the forward and reverse primers tile the first and second region of interest, respectively, at intervals of up to about 100 base pairs.

When more than two regions of interest are targeted, each region can be tiled using pools or sets of primers in the same way.

The selective PCR primers can be specific to different sequences in the corresponding regions of interest, wherein the different sequences in a given region of interest do not overlap with each other.

The disclosure also provides pools or sets of selective PCR primers (optionally as part of a kit), wherein the pool or set comprises at least 20, at least 50 or at least 100 different forward primers and/or at least 20, at least 50 or at least 100 different reverse primers. In a preferred embodiment, the pool or kit comprises at least 20 different selective PCR forward primers and at least 20 different selective PCR reverse primers. More primers can be included for targeting larger and/or multiple regions of interest in a single reaction, for example at least 200 different forward and reverse selective PCR primers may be present.

In one embodiment, the pool or kit of primers comprises:
a. a set of at least 20 forward primers, wherein the forward primers are specific for a first region of interest, and wherein each member of the set of primers targets a different DNA sequence in the first region of interest, and optionally wherein there are multiple copies of each member for the set of forward primers; and
b. a set of at least 20 reverse primers, wherein the reverse primers are specific for a second region of interest, and wherein each member of the set of primers targets a different DNA sequence in the second region of interest, and optionally wherein there are multiple copies of each member for the set of reverse primers;
wherein the first and second regions of interest are different. Preferably, the forward primers further comprising a first universal primer binding site and the reverse primers further comprise a second universal primer binding site. The first and second primer binding sites are different from each other.

Multiple copies of each type of primer may be present in the pool or kit.

The kit may comprise multiple sets of selective PCR primers. For example, in one embodiment, the kit comprises at least 3 sets of primers, at least one of which is a set of forward primers and at least one of which is a set of reverse primers. Each set of primers comprises a plurality of primers that tile a region of interest, as discussed elsewhere. Each region of interest may be different. In some embodiments, the kits comprise at least 4, at least 5, at least 6, at least 7, at least 9, at least 9 or at least 10 pools of primers, each specific for a different region of interest. In one embodiment, the kit comprises at least 5 pools of forward selective PCR primers and at least 5 pools of reverse selective PCR primers.

The sets of selective PCR primers generally will target regions of interest that are suspected of having undergone a genomic rearrangement. In some cases, a set of forward selective PCR primers in one pair of forward and reverse primer sets may act as a set of reverse selective PCR primers in another pair of forward and reverse primer sets.

In some embodiments, the selective PCR primers target a gene fusion. At least one pair of forward and reverse primers may anneal to a DMOI within 500 base pairs from each other, or within 400 base pairs from each other, or within 300 base pairs from each other, or within 200 or within 175 base pairs from each other when a genomic rearrangement, such as a gene fusion, is present.

In one embodiment, there is provided a kit of primers comprising at least one set of primers that target a region of interest in the ROS1 gene, at least one set of primers that target a region of interest that is a potential fusion partner for the ROS1 gene, at least one set of primers that target the ALK gene, and at least one set of primers that target a region of interest that is a potential fusion partner for the ALK gene.

In one embodiment, there is provided a kit of primers comprising at least four sets of primers, wherein the four sets of primers target ALK, ROS1, RET and NTRK1. In another embodiment, there is provided a kit of primers comprising at least 16 sets of primers that target ALK, EML4, ROS1, CD74, SLC34A2, SDC4, EZR, RET, KIF5b, CCDC6, NCOA4, TRIM33, NTRK1, MPRIP, SQSTM1 and TPM3. Each set of primers targets a different gene.

In some embodiments, the selective PCR primers in the kit or primer pools or sets are gene specific primers. The different sets of selective PCR primers may be specific for different genes.

Each selective PCR primer of the kit or pool comprises a region-specific sequence and may optionally comprise an adaptor sequence and/or a UPS. The adaptor sequence is an adaptor sequence for sequencing the amplicons from the PCR.

Preferably, each selective PCR primer of the kit or pool comprises a region-specific sequence and a universal primer binding site. In some embodiments, the kit or pool further comprises additional forward and reverse primer pairs specific to the universal primer sites on the selective PCR primers specific to the regions of interest. In such embodiments, when provided as a kit, the additional forward and reverse primer pairs may be disposed separately from the selective PCR primers. Additionally, the additional primers in the second PCR comprise a UPS-specific sequence and an adaptor sequence for sequencing the amplicons from the selective PCR.

As noted, the methods disclosed herein can be used to target multiple regions of interest and hence multiple possible genomic rearrangements. Not only can the methods be used to detect any kind of possible fusion between two regions of interest (i.e. at any point along their sequence, even without prior knowledge of the location of the rearrangement), but fusions between different regions (e.g. genes) can be detected in a single reaction by including multiple sets of primers. Each primer set will tile a given region of interest, with each primer set targeting a different region. Multiple sets of forward and reverse primers can be included. Whilst each set will generally target a different region, what is considered a forward primer set for one possible genomic rearrangement event could be a reverse primer set of a different genomic rearrangement event.

In some embodiments, the kits include instructions for use, in particular instructions relating to the methods disclosed herein.

Of course, the kits and pools disclosed herein can be used in the methods disclosed herein. Furthermore, the primer information databases may comprise the relevant information for all of the primers in the primer pools disclosed herein.

In a very specific embodiment there is provided a method comprising the following steps:
1. 10 ml of blood is collected into Cell-Free DNA BCT Streck blood tubes.
2. Blood is processed to plasma using methods known in the art
3. DNA is extracted from plasma using QIAamp Circulating Nucleic Acid Kit (Qiagen) following manufactures protocols
4. DNA is quantified by digital droplet PCR to determine the copies of cfDNA within the sample
5. Selective PCR with primer pools targeting rearrangement (i.e. EML4-ALK) is performed on DNA sample. Primer pool also contains 18 primer pairs targeting regions with known population SNPs.
   Selective PCR is performed on two replicates of the same sample.
6. Amplicons generated from step 5 are purified using SPRISelect (Beckman Coulter) following manufactures protocols.
7. A 2$^{nd}$ PCR is performed using primers targeting the UPS attached in Step 5. These primers also contain sample barcodes/indexes which are used for sample identification.
   This step further amplifies the products of Step 5
8. Amplicons generated from Step 7 are purified using SPRISelect
9. Samples are pooled together into a single reaction tube to generate a pool library
10. A region between 200-350 bp is size selected using the Pippin Prep System (Sage Science)
11. Library from Step 10 is quantified using Library Quantification Kit (KAPA Biosystems)
12. Quantified pooled library is sequenced on NextSeq Platform using 300 Cycles of sequencing Analysis
13. Samples are de-multiplexed—Indexes are used to identify unique samples
14. Analysis pipeline performed (details to follow)
15. Fusion breakpoint is called depending on weak/strong anchor methodology
16. Patient specific report is generated indicating presence/absence of Fusion and indicating treatments/trials relevant to the genetic alteration The present disclosure provides a method for detecting genomic rearrangements, including gene fusions, comprising:
a. providing a patient blood sample comprising ctDNA;
b. extracting the ctDNA from the sample;
c. conducting a selective multiplex PCR on the extracted ctDNA using a pool of at least 20 forward primers specific for a first gene and a pool of at least 20 reverse primers specific for a second gene, wherein the pool of forward primers tiles a first gene (or a region thereof) and the pool of reverse primers tile a second gene (or a region thereof), with spaces of between 50 and 100 nucleotide bases between adjacent primers in the pools, wherein the PCR incorporates universal primer binding sites into the amplicons that are generated;
d. conducting a further PCR using primers specific for the universal primer binding sites incorporated in step c.;
e. sequencing the amplification product from step d.; and
f. determining the presence or absence of a genomic rearrangement according to the sequence of the amplification product.

The preferred features for the second and subsequent aspects are as provided for the first aspect, mutatis mutandis.

The present invention will now be further explained by reference to a number of non-limiting examples.

EXAMPLES

Aspects of the present teachings can be further understood in light of the following examples, which should not be construed as limiting the scope of the present teachings in any way.

Example 1: Detection of EML4-ALK Variant at a Range of Allelic Fractions

A custom cell free DNA reference standard containing an EML4-ALK fusion of sequence (SEQ ID NO: 1)
GAAGTTCCTATACTTTCTAGAGAATAGGAACTTC at an allelic fraction of 2.5% was obtained from Horizon Discoveries. This reference standard was diluted in sheared (average 188 bp) human placental DNA (Bioline) to achieve allelic fractions of 1%, 0.5%, 0.25%, 0.125% and 0.0625%. Three samples were created at each allelic fraction.

Each sample was split into two replicates, each containing a total of 4000 input copies. PCR amplification was performed on two replicates using the ALK primer panel. Each PCR contained 25 uL DNA, 27.5 uL Platinum SuperFi 2× Master Mix (Invitrogen) and 2.5 uL of the ALK primer pool. PCR cycling was followed using manufacturer' instructions. The PCR product was cleaned up using SPRIselect reagent (Beckman Coulter B23319) using the manufacturers protocol. DNA was eluted in 18 uL and a second PCR using Indexed illumina primers was performed. Each PCR contained 15 uL DNA, 17.5 uL Platinum SuperFi 2× Master Mix (Invitrogen) and 2.4 uL Indexed illumina primers. PCR Cycling was followed using manufactures instructions. The PCR product was cleaned up once using SPRIselect reagent (Beckman Coulter B23319) using the manufacturers protocol. indexes samples from different replicates were pooled into a tube containing 10 uL 10 mM Tris-HCl pH 8. Samples were selected for 195-350 bp using a 2% Agarose Dye Free cassette and marker L on the Pippin Prep (Sage Science), following the manufacturer's instructions. Size selected DNA was quantified by qPCR using a KAPA Library quantification kit (KAPABIOSYSTEMS), following the manufacturer's instructions. Quantified libraries were sequenced on the NextSeq500 Illumina platform and data analysis was performed.

Figure 2:
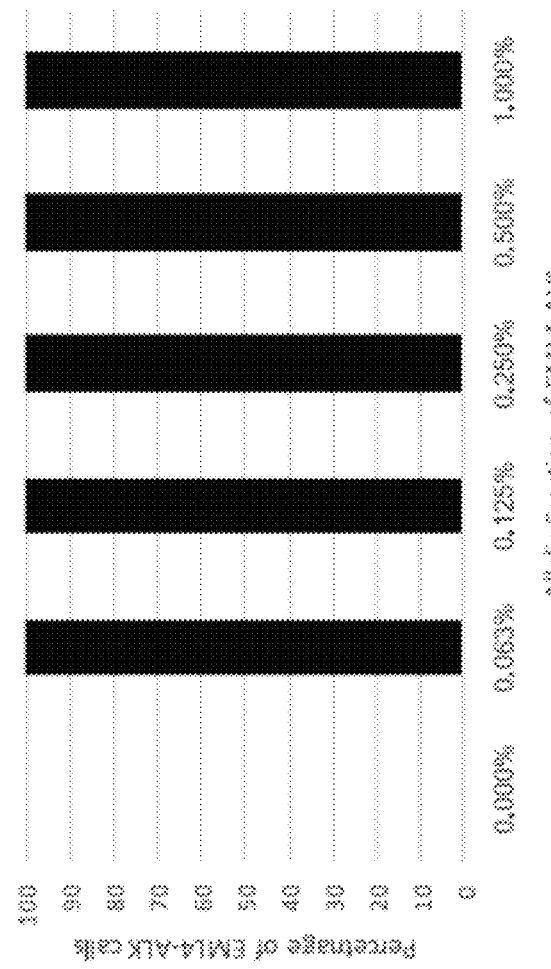
FIG. 2: The sequence of the EML4-ALK gene fusion in the fusion-positive material from Horizon is known (expected EML4-ALK breakpoint). A. Different combinations of adjacent primers are able to amplify the gene fusion. Two types of reads, containing the fusion breakpoint, are obtained as a result of amplification of the fusion by different primer pairs. Both reads contain the expected fusion gene sequence as well as flanking DNA sequences of different lengths. From top to bottom: SEQ ID NOS: 1, 2, and 3. B. Fusion detection was performed on three replicates at each of the allelic frequencies. Fusions were detected at all allelic fractions in all replicates.
Figure 3:
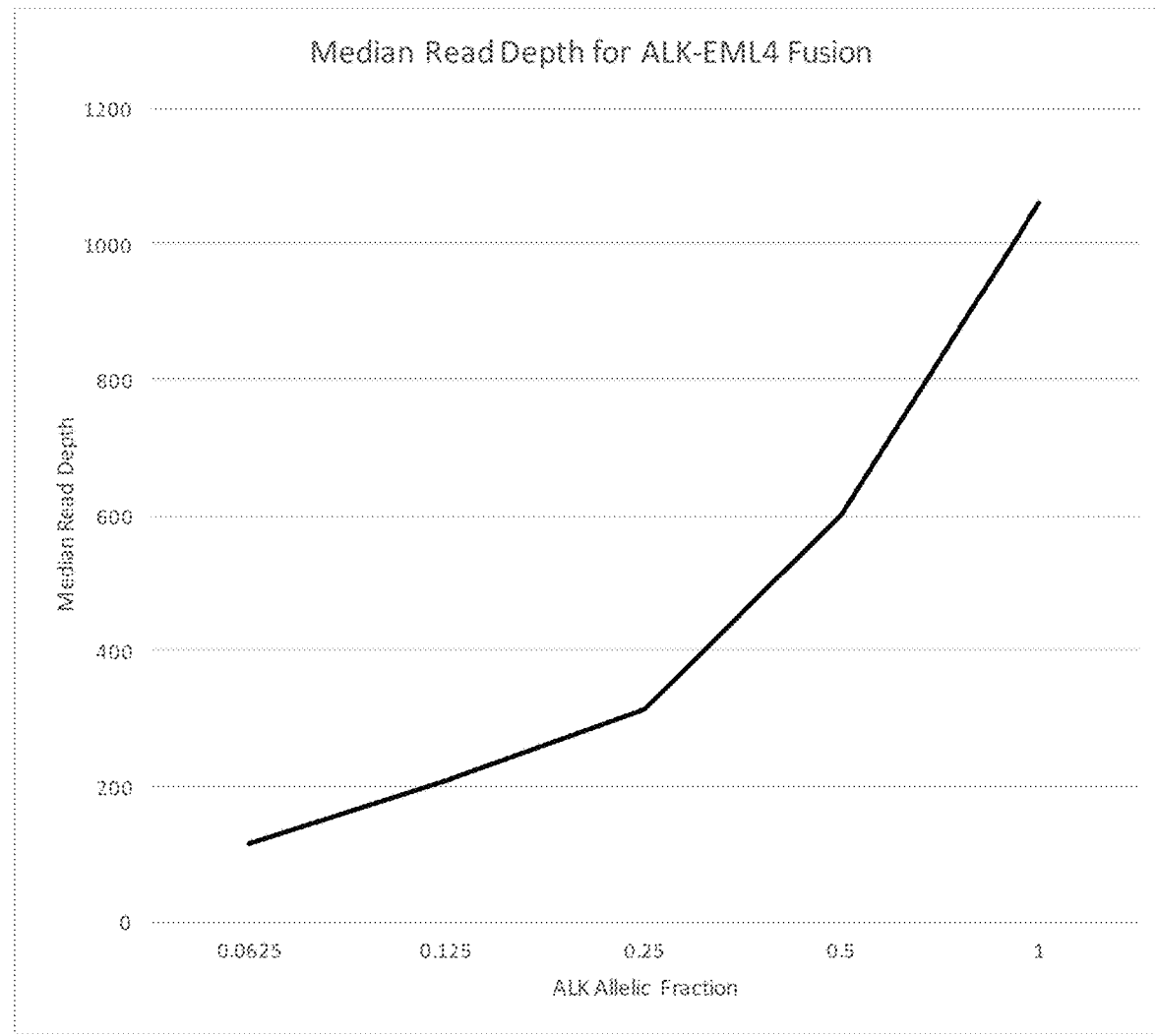
FIG. 3: Median read depth obtained for an ALK-EML4 fusion at 0.0625, 0.125, 0.25, 0.5 and 1% allelic fraction. The median of the number of fusion reads detected in the three replicates was calculated and plotted against the different allelic fractions.

EML4-ALK enrichment using Selective PCR and Next generation sequencing (FIG. 1). The EML4-ALK fusion variant was detected at all allelic fractions tested (FIG. 2); illustrating that selective PCR consistently amplifies as little as 2.5 molecules of Fusion DNA as indicated by 100% detection at 0.0625% AF (4000 input copies). The sequence obtained by the selective PCR method matched the expected breakpoint (FIG. 2A), indicating the selective nature of the method. Specificity of the method is at 100% with no additional Fusions detected in any of the samples tested and with no fusion calls being made in samples that don't contain Fusion DNA (0% AF). The median read depth of the ALK-EML4 fusion (FIG. 3), at a range of AFs, shows a decrease in reads obtained by selective PCR that correlates with a decrease in AF, indicating linear amplification of the gene fusion.

Example 2: Detection of ROS1-CD74 Variant

A synthetic gBlock containing a ROS1 fusion sequence (based on a sequence reported in the literature: Seki, Mizukami and Kohno, *Biomolecules*, 2015, 5, 2464-2476) was synthesized by IDT and was sheared using the covaris to achieve an average size of 150 bp. The gBlock was added to sheared (average 188 bp) human placental DNA (Bioline) to achieve an allelic fraction of 1%.

Each sample was split into two replicates, each containing a total of 4000 input copies. PCR amplification was performed on two of the replicates using the ROS1 primer panel. Each PCR contained 25 uL DNA, 27.5 uL Platinum SuperFi 2× Master Mix (Invitrogen) and 2.5 uL of the ROS1 primer pool. PCR Cycling was followed using manufactures instructions. The PCR product was cleaned up using SPRIselect reagent (Beckman Coulter B23319) using the manufacturers protocol. DNA was eluted in 18 uL and a second PCR using Indexed illumina primers was performed. Each PCR contained 15 uL DNA, 17.5 uL Platinum SuperFi 2× Master Mix (Invitrogen) and 2.4 uL Indexed illumina primers. PCR Cycling was followed using manufactures instructions. The PCR product was cleaned up once using SPRIselect reagent (Beckman Coulter B23319) using the manufacturers protocol. indexes samples from different replicates were pooled into a tube containing 10 uL 10 mM Tris-HCl pH 8. Samples were selected for 195-350 bp using a 2% Agarose Dye Free cassette and marker L on the Pippin Prep (Sage Science), following the manufacturer's instructions. Size selected DNA was quantified by qPCR using a KAPA Library quantification kit (KAPABIOSYSTEMS), following the manufacturer's instructions. Quantified libraries were sequenced on the NextSeq500 Illumina platform and data analysis was performed.

Figure 4:
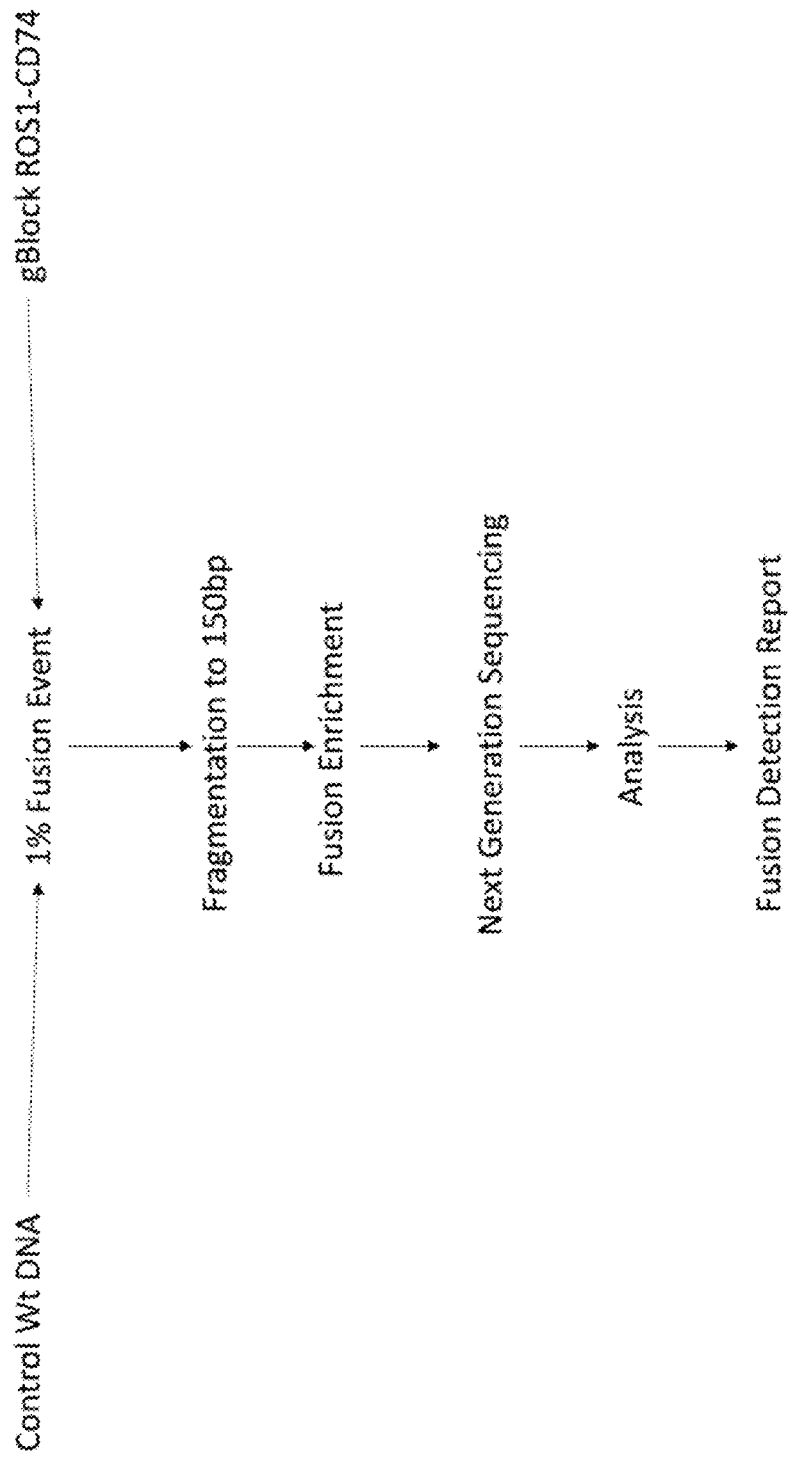
FIG. 4: Experiment determining ROS1 Fusion. To test the detection of fusion genes between ROS1 and CD74, a 500 bp fragment of synthetic DNA (gblock) that contains the sequence of a published ROS1-CD74 gene fusion was synthesized by IDT. The synthetic gblock was fragmented by sonication (Covaris) to an average of 150 bp and added to sheared fusion-negative human placental DNA to achieve an allelic fraction of 1% at 4000 input copies. The fusion gene was amplified by selective PCR and decoded on the NextSeq500 (Illumina). Sequencing data is screened for the presence of fusion genes using the described bioinformatic pipeline and data is published in a fusion detection report.

ROS1-CD74 enrichment using selective PCR and Sequencing on the NextSeq platform (FIG. 4). The sequence of the ROS1-CD74 fusion breakpoint is known in the field (Seki, Mizukami and Kohno, *Biomolecules*, 2015, 5, 2464-2476) and was synthesised into a double stranded DNA fragment (FIG. 5). The method detected the fusion breakpoint with two primer pairs, CD74_E6-I6_10/ROS1_I32_E33_414 and CD74_E6-I6_9/ROS1_I32_E33_414 (FIG. 6A). The sequence read of both primer pairs matched that of the synthesised published ROS1-CD74 breakpoint (FIG. 6B). The sequence read obtained for each primer pair is shown and is a 100% match with the published breakpoint; highlighting that the selective PCR method can amplify a fusion breakpoint with multiple primer combinations and can accurately identify the sequence of a fusion breakpoint.

Example 3: Detection of ROS1-CD74 Variant Using Sequential Amplification

The same synthetic ROS1 fusion gBlock at 1% allelic fraction as was used in Example 2 was tested. Each sample was split into two replicates, each containing a total of 4000 input copies. Linear amplification of the template was performed on two of the replicates using only the ROS1 forward primer panel. Each reaction contained 25 uL DNA, 27.5 uL Platinum SuperFi 2× Master Mix (Invitrogen) and 2.5 uL of the ROS1 forward primer pool. Cycling was followed using manufactures instructions. The PCR product was cleaned up once using SPRIselect reagent (Beckman Coulter B23319) using the manufacturers protocol. DNA was eluted in 18 uL and a first PCR using a i5 adapter forward primer and the ROS1 reverse primer pool was performed. Each PCR contained 10 uL DNA, 25 uL Platinum SuperFi 2× Master Mix (Invitrogen), 2.5 ul of the i5 adapter forward primer and 2.5 uL of the ROS1 reverse primer pool. Cycling was followed using manufactures instructions. The PCR product was cleaned up once using SPRIselect reagent (Beckman Coulter B23319) using the manufacturers protocol. DNA was eluted in 18 uL and a second PCR using Indexed illumina primers was performed. Each PCR contained 15 uL DNA, 17.5 uL Platinum SuperFi 2× Master Mix (Invitrogen) and 2.4 uL Indexed illumina primers. PCR Cycling was followed using manufactures instructions. The PCR product was cleaned up once using SPRIselect reagent (Beckman Coulter B23319) using the manufacturers protocol. Indexed samples from different replicates were pooled into a tube containing 10 uL 10 mM Tris-HCl pH 8. Samples were selected for 195-350 bp using a 2% Agarose Dye Free cassette and marker L on the Pippin Prep (Sage Science), following the manufacturer's instructions. Size selected DNA was quantified by qPCR using a KAPA Library quantification kit (KAPABIOSYSTEMS), following the manufacturer's instructions. Quantified libraries were sequenced on the NextSeq500 Illumina platform and data analysis was performed.

Example 4: Matching Sequences to a Reference Database

Once sequence reads have been demultiplexed, adaptors have been trimmed and reads have been merged, they are compared against a database of all primers used in the fusion assay. Any sequencing reads containing the sequence of a primer designed to a 5' partner at the start and that of a 3' partner at the end are identified as potential fusion reads and carried forward for further analysis. The table of primers also contains a list of the expected sequences downstream from each primer (based on the primer bind site in the targeted region as opposed to another part of the genome) and the number of bases that need to match following the end of the primer in order to attain either low or high confidence that the sequence being read belongs to the potential fusion partner. A fusion may be called when the sequence from at least one side is identified with high confidence as belonging to a possible fusion partner (e.g. ELM4) and the other side is identified as belonging with at least low confidence to a fusion partner (e.g. ALK). A fusion might be only called if this is either detected in duplicate reactions or if there are 2 or more reads where both sides are high confidence.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. cfDNA analysis) those skilled in the art will recognize that its usefulness is not limited thereto and that the present invention can be beneficially utilized in any number of environments and implementations where it is desirable to examine other samples. Accordingly, the claims set forth below should be construed in view of the full breadth and spirit of the invention as disclosed herein.

The invention claimed is:

1. A method for identifying a genomic fusion, comprising:
   (a) performing a fusion-specific polymerase chain reaction (PCR) on circulating cfDNA (cell-free DNA) from a subject using a plurality of forward primers and a plurality of reverse primers, wherein the plurality of forward primers hybridizes to the same strand of a first region of a reference human genome and the plurality of reverse primers hybridizes to the same strand of a second region of a reference human genome, to produce amplification products, wherein the first and second regions are on different chromosomes or are on the same chromosome but spaced apart by at least 10 kb, and wherein:
   i. each forward primer comprises a sequence at the 3' end that specifically hybridize to the first region of the reference human genome and a 5' tail that provides binding site for a first primer; and
   ii. each reverse primer comprises a sequence at the 3' end that specifically hybridizes to the second region the reference human genome and a 5' tail that provides a binding site for a second primer;
   (b) performing a second PCR on the amplification products produced in the fusion-specific PCR of step (a) using the first primer and the second primer;
   (c) sequencing the amplification products produced in step (b) to produce sequence reads; and
   (d) identifying sequence reads that correspond to a fusion between the first and second regions by:
      (i) identifying which of the sequence reads have the sequence of a forward primer used in step (a), or complement thereof, at one end and the sequence of a reverse primer used in step (a), or a complement thereof, at the other end;
      (ii) for each sequence read identified in (d)(i), determining whether the sequence read comprises a sequence that matches a sequence in the first region of the reference human genome; and
      (iii) for each sequence read identified in (d)(i), determining whether the sequence read comprises a sequence that matches a sequence in the second region of the reference human genome;
   wherein a PCR product that corresponds to a fusion comprises the sequence of a forward primer used in step (a) at one end and the sequence of a reverse primer used in step (a) at the other end, a sequence that matches a sequence in the first region of the reference human genome, and a sequence that matches a sequence in the second region of the reference human genome.

2. The method of claim 1, wherein:
   step (d)(ii) comprises, for each sequence read identified in (d)(i), determining whether the sequence read comprises a sequence that matches a sequence that is immediately adjacent to the sequence of the forward primer of the sequence read in the first region of the reference human genome; and step (d)(iii) comprises, for each sequence read identified in (d)(i), determining whether the sequence read comprises a sequence that matches a sequence that is immediately adjacent to the sequence of the reverse primer of the sequence read in the second region of the reference human genome.

3. The method of claim 2 wherein:
   step (d)(ii) comprises determining whether the sequence in the sequence read has sufficient base pairs that uniquely match or does not have sufficient base pairs that uniquely match to the sequence that is downstream from sequence of the forward primer in the reference genome; and
   step (d)(iii) comprises determining whether the sequence in the sequence read has sufficient base pairs that uniquely match or does not have sufficient base pairs that uniquely match to the sequence that is downstream from sequence of the reverse primer of the sequence read in the reference genome.

4. The method of claim 3, wherein:
   i. the sequence read has sufficient base pairs that uniquely match when the sequence immediately downstream from the sequence of the primer in the sequence read matches only the sequence immediately downstream from the sequence of the primer in the reference genome; and
   ii. the sequence read does not have sufficient base pairs that uniquely match when the sequence immediately downstream from the sequence of the primer in the sequence read matches the sequence immediately downstream from the sequence of the primer in the reference genome as well as other sequences in the reference genome.

5. The method of claim 3, wherein a sequence read that corresponds to a fusion comprises the sequence of a forward primer used in step (a) at one end and the sequence of a reverse primer used in step (a) at the other end; a sequence that has sufficient base pairs that uniquely match to a sequence in the first region of the reference human genome; and a sequence that has sufficient base pairs that uniquely match to a sequence in the second region of the reference human genome.

6. The method of claim 3, wherein a sequence read that corresponds to a fusion comprises the sequence of a forward primer used in step (a) at one end and the sequence of a reverse primer used in step (a) at the other end, a sequence that has sufficient base pairs that uniquely match to a sequence in the first region of the reference human genome, and a sequence that has sufficient base pairs that uniquely match to a sequence in the second region of the reference human genome, only if the same sequence is observed in a replicate fusion-specific PCR reaction.

7. The method of claim 1, wherein:
   i. the plurality of forward primers comprises at least 20 primers;
   ii. the plurality of reverse primers comprises at least 20 primers.

8. The method of claim 1, wherein the first region is a kinase gene and the second is fusion partner for the kinase gene.

9. The method of claim 8, wherein the kinase gene is the ALK gene and the potential fusion partner for the kinase gene is the EML4 gene.

10. The method of claim 8, wherein the kinase gene is the RET gene and the potential fusion partner for the kinase gene is the TRIM33, CCDC6, KIF5B and NCOA4 genes.

11. The method of claim 8, wherein the kinase gene is the ROS1 gene and the potential fusion partner for the kinase gene is the CD74, SLC34A2 and SDC4 genes.

12. The method of claim 8, wherein the kinase gene is the NTRK1 gene and the potential fusion partner for the kinase gene is the TPM3, SQSTM1, CD74 or MPRIP gene.

* * * * *